US012629078B2

(12) United States Patent
Jing et al.

(10) Patent No.: US 12,629,078 B2
(45) Date of Patent: May 19, 2026

(54) ELECTRONIC DEVICE

(71) Applicant: GUANGDONG OPPO MOBILE TELECOMMUNICATIONS CORP., LTD., Dongguan (CN)

(72) Inventors: Xiaohong Jing, Dongguan (CN); Wei Fan, Dongguan (CN); Yuege Xue, Dongguan (CN)

(73) Assignee: GUANGDONG OPPO MOBILE TELECOMMUNICATIONS CORP., LTD., Dongguan (CN)

( * ) Notice: Subject to any disclaimer, the term of this patent is extended or adjusted under 35 U.S.C. 154(b) by 543 days.

(21) Appl. No.: 18/146,690

(22) Filed: Dec. 27, 2022

(65) Prior Publication Data

US 2023/0157608 A1     May 25, 2023

Related U.S. Application Data

(63) Continuation of application No. PCT/CN2021/097023, filed on May 29, 2021.

(30) Foreign Application Priority Data

Aug. 17, 2020    (CN) .......................... 202021719904.7

(51) Int. Cl.
    *A61B 5/282*        (2021.01)
    *A61B 5/256*        (2021.01)
    *A61B 5/339*        (2021.01)

(52) U.S. Cl.
    CPC .............. *A61B 5/282* (2021.01); *A61B 5/256* (2021.01); *A61B 5/339* (2021.01); *A61B 2562/164* (2013.01); *A61B 2562/166* (2013.01)

(58) Field of Classification Search
    CPC .... A61B 5/282; A61B 5/256; A61B 2562/166
    See application file for complete search history.

(56) References Cited

U.S. PATENT DOCUMENTS 10,729,347  B1     8/2020  Schleicher
2018/0098731  A1     4/2018  Yoon et al.
(Continued)

FOREIGN PATENT DOCUMENTS

CN        205015630        2/2016
CN        106388809        2/2017
(Continued)

OTHER PUBLICATIONS

EPO, Extended European Search Report for EP Application No. 21857275.8, Dec. 18, 2023.
(Continued)

*Primary Examiner* — Linda C Dvorak
*Assistant Examiner* — William Mossbrook
(74) *Attorney, Agent, or Firm* — Hodgson Russ LLP

(57)        ABSTRACT

An electronic device includes a housing, a first electrocardiograph (ECG) electrode, a second ECG electrode, an ECG circuit board, and a conductive resilient sheet. The housing includes a back cover and a middle frame fixed with the back cover. The first ECG electrode is disposed at the back cover. The second ECG electrode is disposed at the middle frame. The ECG circuit board is disposed inside the back cover and inside the middle frame, and provided with a first branch electrically connected with the first ECG electrode and a second branch disposed adjacent to and extending toward the second ECG electrode. The conductive resilient sheet is fixed inside the middle frame and configured to make the second ECG electrode and the second branch be in a conducting state. The conductive resilient sheet is provided to make the second ECG electrode and the second branch be in a conducting state.

12 Claims, 21 Drawing Sheets

(56)          References Cited

U.S. PATENT DOCUMENTS

| | | |
|---|---|---|
| 2019/0059756 A1 | 2/2019 | Rasmussen et al. |
| 2019/0072912 A1* | 3/2019 | Pandya ............. A61B 5/02438 |
| 2019/0223791 A1 | 7/2019 | Sayani et al. |

FOREIGN PATENT DOCUMENTS

| | | | |
|---|---|---|---|
| CN | 106901721 | 6/2017 | |
| CN | 107706578 | 2/2018 | |
| CN | 209674200 | 11/2019 | |
| CN | 209789844 | 12/2019 | |
| CN | 110794666 | 2/2020 | |
| CN | 210784331 | 6/2020 | |
| CN | 211022649 | 7/2020 | |
| EP | 3451117 | 3/2019 | |
| WO | WO-2021128286 A1 * | 7/2021 | .......... H04M 1/0262 |

OTHER PUBLICATIONS

WIPO, International Search Report and Written Opinion for International Application No. PCT/CN2021/097023, Aug. 5, 2021.
EPO, Communication for EP Application No. 21857275.8, Jul. 14, 2025.

* cited by examiner

ELECTRONIC DEVICE

CROSS-REFERENCE TO RELATED APPLICATION(S)

This application is a continuation of International Application No. PCT/CN2021/097023, filed May 29, 2021, which claims priority to Chinese Patent Application No. 202021719904.7, filed Aug. 17, 2020, the entire disclosures of which are incorporated herein by reference.

TECHNICAL FIELD

The disclosure relates to the field of communication devices, in particular, to an electronic device.

BACKGROUND

A smart watch is usually provided with an electrocardiograph (ECG) electrode on the back thereof and a touch electrode on a side face thereof, and the ECG electrode is configured to contact a wrist of a user. A circuit conduction path connecting the ECG electrode and the touch electrode may be disposed inside the smart watch. The circuit conduction path is configured to make the ECG electrode and the touch electrode be in a conducting state, facilitating obtaining an electrocardiogram of the user. However, the circuit conduction path connecting the ECG electrode and the touch electrode has a complex structure, resulting in insensitive ECG detection and poor user experience.

SUMMARY

An electronic device is provided in the disclosure. The electronic device includes a housing, a first electrocardiograph (ECG) electrode, a second ECG electrode, an ECG circuit board, and a conductive resilient sheet. The housing includes a back cover and a middle frame fixed with the back cover. The first ECG electrode is disposed at the back cover. The second ECG electrode is disposed at the middle frame. The ECG circuit board is disposed inside the back cover and inside the middle frame, and provided with a first branch electrically connected with the first ECG electrode and a second branch disposed adjacent to and extending toward the second ECG electrode. The conductive resilient sheet is fixed inside the middle frame and configured to make the second ECG electrode and the second branch be in a conducting state.

BRIEF DESCRIPTION OF THE DRAWINGS

To describe the technical solutions in the implementations of the disclosure more clearly, the following briefly introduces the accompanying drawings required for describing the implementations. Apparently, the accompanying drawings in the following description illustrate some implementations of the disclosure. Those of ordinary skill in the art may also obtain other drawings based on these accompanying drawings without creative efforts.

DETAILED DESCRIPTION

Figure 1:
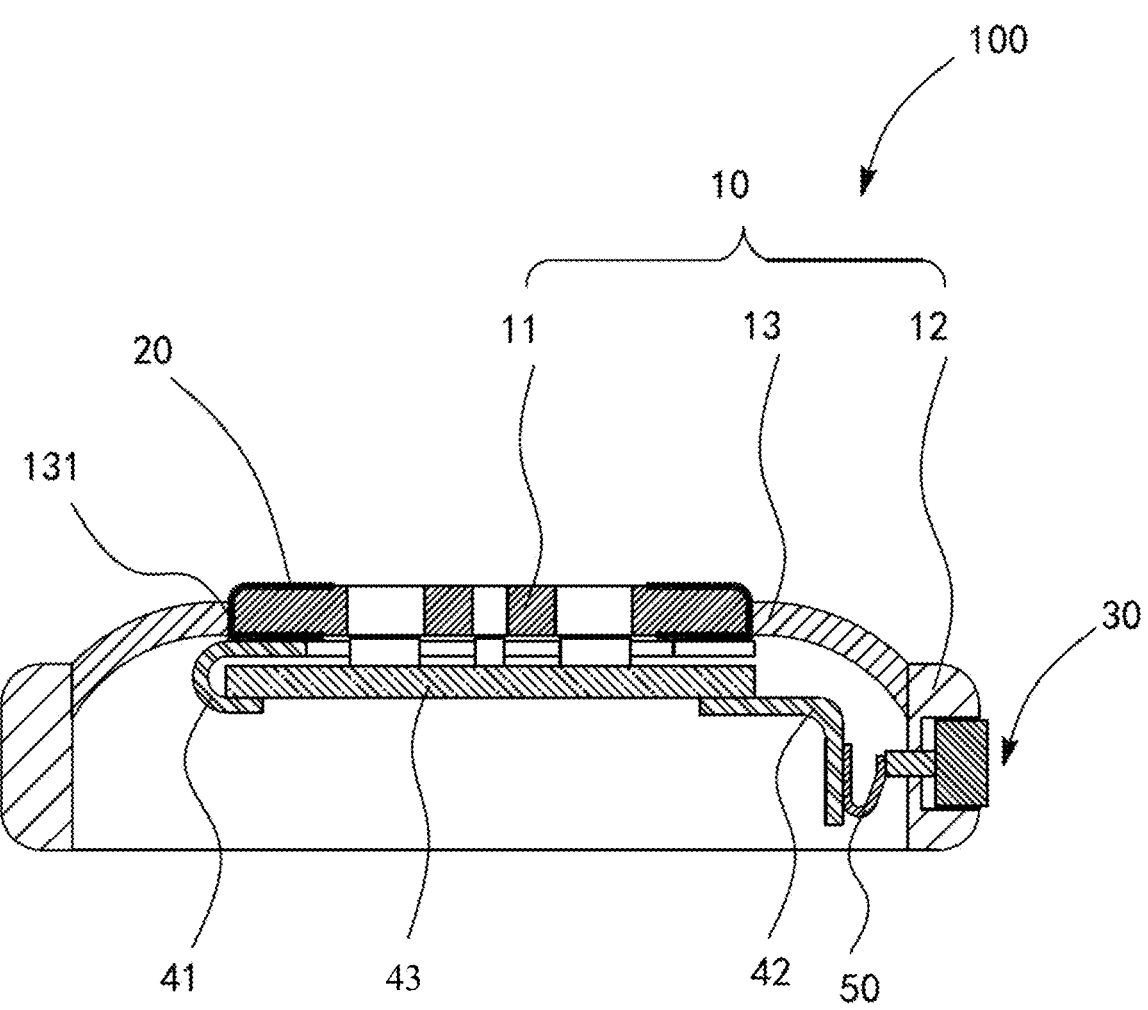
FIG. 1 is a schematic partial cross-sectional view of an electronic device provided in an implementation of the disclosure.

The technical solutions in the implementations of the disclosure are clearly and completely described in the following with reference to the accompanying drawings in the implementations of the disclosure.

An electronic device is provided in implementations of the disclosure. The electronic device includes a housing, a first electrocardiograph (ECG) electrode, a second ECG electrode, an ECG circuit board, and a conductive resilient sheet. The housing includes a back cover and a middle frame fixed with the back cover. The first ECG electrode is disposed at the back cover. The second ECG electrode is disposed at the middle frame. The ECG circuit board is disposed inside the back cover and inside the middle frame, and provided with a first branch electrically connected with the first ECG electrode and a second branch disposed adjacent to and extending toward the second ECG electrode. The conductive resilient sheet is fixed inside the middle frame and configured to make the second ECG electrode and the second branch be in a conducting state.

In an implementation, the electronic device further includes a side-button circuit board fixed inside the middle frame, where the conductive resilient sheet is fixedly connected with the side-button circuit board.

In an implementation, the conductive resilient sheet is fixedly connected with the second branch.

In an implementation, the electronic device further includes a side button connected with the middle frame and being pressable, where the side-button circuit board is provided with a button switch corresponding to the side button.

In an implementation, the second ECG electrode is disposed in the side button.

In an implementation, the second ECG electrode and the side button are arranged side by side and spaced apart from each other.

In an implementation, the conductive resilient sheet is provided with a fixed base close to the button switch and attached to the side-button circuit board and a resilient arm extending from the fixed base in a bent way, and an end portion of the resilient arm faces the button switch and resiliently abuts against the side button.

In an implementation, the conductive resilient sheet is also provided with a branch base extending from the fixed base and a branch resilient arm extending from the branch base in a bent way, and the branch base is attached to the side-button circuit board, and the branch resilient arm resiliently abuts against the second branch.

In an implementation, the branch base is provided with two limit buckles opposite each other, an end portion of the branch resilient arm is limited between the two limit buckles and provided with a limit protrusion that is clamped by the two limit buckles, so that the branch resilient arm is prevented from generating plastic deformation.

In an implementation, the conductive resilient sheet is also provided with a branch conductive resilient sheet that is fixed to the side-button circuit board and spaced apart from the fixed base, and the branch conductive resilient sheet and the fixed base are in a conducting state via the side-button circuit board, and the branch conductive resilient sheet elastically resists against the second branch.

In an implementation, the second ECG electrode is disposed at a button cap of the side button, the side button is also provided with a button column fixedly connected with the second ECG electrode, the button column and the second ECG electrode are in a conducting state, and the button column resiliently abuts against the end portion of the resilient arm and is configured to trigger the button switch when the second ECG electrode is pressed.

In an implementation, the second ECG electrode is provided with a touch panel disposed outside the middle frame and a conductive column extending from the touch panel, the touch panel serves as the button cap of the side button, and the conductive column resiliently abuts against the end portion of the resilient arm and is configured to trigger the button switch when the touch panel is pressed.

In an implementation, the side-button circuit board and the middle frame cooperatively define a gap therebetween, and an end portion of the second branch away from a printed circuit board (PCB) substrate of the ECG circuit board is disposed within the gap between the side-button circuit board and an inner wall of the middle frame.

In an implementation, the side-button circuit board is attached to an inner wall of the middle frame, an end portion of the second branch away from a PCB substrate of the ECG circuit board is attached to a side surface of the side-button circuit board away from the middle frame, part of the conductive resilient sheet is disposed on the side surface of the side-button circuit board away from the middle frame and connected with the second branch, and another part of the conductive resilient sheet is disposed on a side surface of the side-button circuit board close to the middle frame and connected with the second ECG electrode.

In an implementation, the ECG circuit board is fixed inside the back cover, the first branch and the second branch extend out two opposite positions on a circumferential side of the ECG circuit board, respectively, and the first branch is bent relative to a PCB substrate of the ECG circuit board and stacked on the back cover.

In an implementation, the second ECG electrode is fixed to the middle frame and partially disposed on an inner wall of the middle frame.

In an implementation, the conductive resilient sheet is fixed to a portion of the second ECG electrode disposed on the inner wall of the middle frame and resiliently abuts against the second branch.

In an implementation, the electronic device includes an ECG chip electrically connected with the first ECG electrode and the second ECG electrode, where the ECG chip is configured to generate ECG data according to electrical signals of the first ECG electrode and the second ECG electrode.

In an implementation, the electronic device further includes a display screen fixed to the middle frame and opposite the back cover, where the display screen is electrically connected with the ECG circuit board and configured to receive the ECG data from the ECG chip via the ECG circuit board and generate a displayable ECG image according to the ECG data.

In an implementation, the back cover is provided with two first ECG electrodes, each of the two first ECG electrodes is in a semi-annular shape, and the two first ECG electrodes cooperatively form a substantially annular shape and disposed on a periphery of the back cover.

The technical solutions in the implementations of the disclosure are clearly and completely described in the following with reference to the accompanying drawings in the implementations of the disclosure to make those skilled in the art better understand the technical solutions of the disclosure. Apparently, the described implementations are merely part rather than all of the implementations of the disclosure. All other implementations obtained by those of ordinary skill in the art based on the implementations of the disclosure without creative efforts are within the scope of the disclosure.

In the implementations of the disclose, it may be understood that terms such as "thickness" referred to herein which indicate directional relationship or positional relationship are directional relationship or positional relationship based on accompanying drawings and are only for the convenience of description and simplicity, rather than explicitly or implicitly indicate that devices or components referred to herein must have a certain direction or be configured or operated in a certain direction and therefore shall not be understood as limitation on the disclosure.

Figure 2:
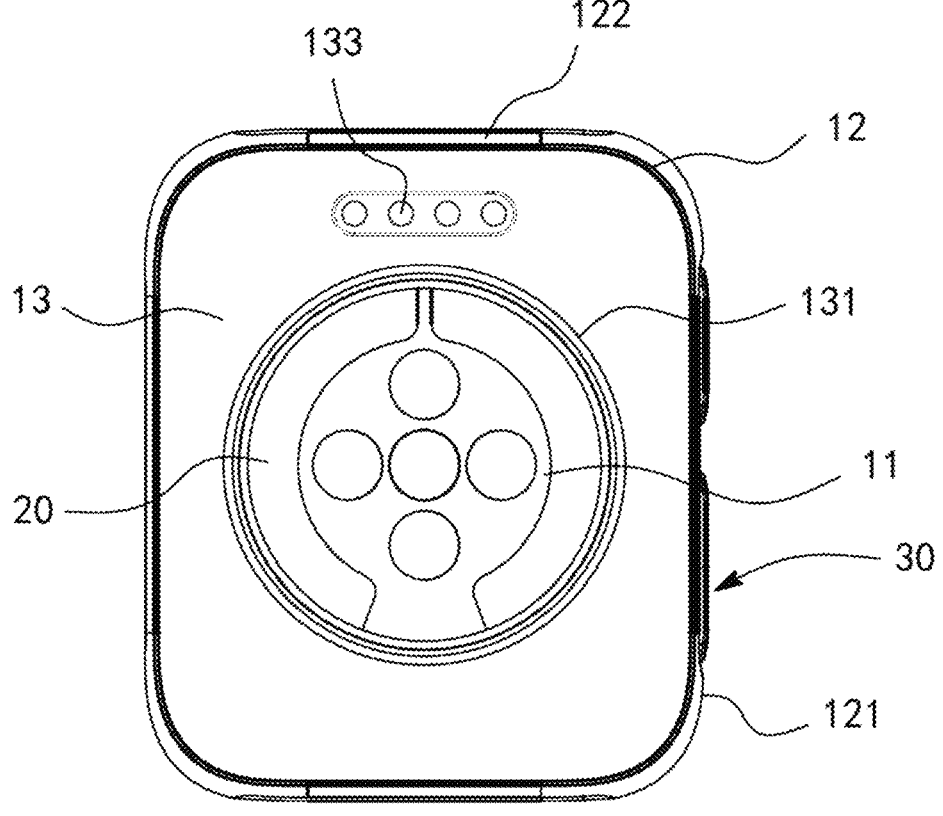
FIG. 2 is a schematic top view of the electronic device provided in the implementation illustrated in FIG. 1.

Refer to FIG. 1 and FIG. 2, an electronic device 100 is provided in the disclosure. The electronic device 100 includes a housing 10, a first electrocardiograph (ECG) electrode 20, a second ECG electrode 30, an ECG circuit board 40, and a conductive resilient sheet 50. The housing 10 includes a back cover 11 and a middle frame 12 fixed with the back cover 11. The first ECG electrode 20 is disposed at the back cover 11. The second ECG electrode 30 is disposed at the middle frame 12. The ECG circuit board 40 is disposed inside the back cover 11 and inside the middle frame 12, and provided with a first branch 41 electrically connected with the first ECG electrode 20 and a second branch 42 disposed adjacent to and extending toward the second ECG electrode 30. The conductive resilient sheet 50 is fixed inside the middle frame 12 and allows for a conduction between the second ECG electrode 30 and the second branch 42. It is noted that, the first ECG electrode 20 and the second ECG electrode 30 are both configured to contact a user, so that the electronic device 100 can obtain ECG data of the user and thus obtain an electrocardiogram according to the ECG data.

The ECG circuit board 40 is provided with the first branch 41 electrically connected with the first ECG electrode 20 and the second branch 42 disposed adjacent to and extending toward the second ECG electrode 30, and the conductive resilient sheet 50 is provided to make the second ECG electrode 30 and the second branch 42 be in a conducting state, so that a closed path between the first ECG electrode 20 and the second ECG electrode 30 can be shortened, thereby improving a sensitivity of obtaining ECG data and user experience. It is noted that, in the implementations of the disclosure, the conductive resilient sheet 50 is configured to make the second ECG electrode 30 and the second branch 42 be in electrical connection with each other.

It may be understood that, in the implementations of the disclosure, a smart watch is taken as an example for illustrating the electronic device 100, but the electronic device 100 is not limited to a smart watch, and may also be other electronic devices. The electronic device 100 may be a wearable device such as a wristband, glasses, a head-mounted device, or goggles that includes the first ECG electrode 20, the second ECG electrode 30, and the ECG circuit board 40, and may also be a terminal device such as a mobile phone, a tablet computer, or a notebook computer that includes the first ECG electrode 20, the second ECG electrode 30, and the ECG circuit board 40. The electronic device 100 of the disclosure may detect the ECG data of the user with aid of the first ECG electrode 20, the second ECG electrode 30, and the ECG circuit board 40, and may obtain the electrocardiogram of the user according to the ECG data. In other words, the first ECG electrode 20 and the second ECG electrode 30 may serve as ECG components.

In the implementations, the housing 10 serves as an external protective component of the electronic device 100 and is used to protect the ECG circuit board 40 and other components inside the electronic device 100. The back cover 11 is disposed on the back of the electronic device 100, and thus when the electronic device 100 is worn on the user, the back cover 11 of the electronic device 100 is at a position where the back cover 11 is readily to contact the skin of the user. If the electronic device 100 is a smart watch, the back cover 11 may be a rear cover of the smart watch. The middle frame 12 may be disposed at a peripheral side of the electronic device 100 for stabilizing and fixing peripheral structures of the electronic device 100. If the electronic device 100 is a smart watch, the middle frame 12 may serve as a structure at a peripheral side of a dial. The middle frame 12 may be provided with control structures, such as a button, a knob, a touch key, and a crown. The middle frame 12 may be but not be limited to a rectangular frame, and may also be a circular frame, a triangular frame, a pentagonal frame, or other polygonal frames. The middle frame 12 has two first sides 121 opposite each other and two second sides 122 opposite each other, and the two second sides 122 are disposed between the two first sides 121. The two first sides 122 of the electronic device 100 may be connected with a watchband, and may be provided with control structures for receiving touch operations of the user.

In an implementation, the housing 10 further includes a rear housing 13 covering the middle frame 12. The rear housing 13 defines a through hole 131, and the back cover 11 covers the through hole 131. The rear housing 13 may be but not be limited to a rectangular plate. The rear housing 13 may also be a circular plate, a triangular plate, a pentagonal plate, or other polygonal plates. The through hole 131 may be but not be limited to a circular opening, and may also be a square opening, a triangular opening, a polygonal opening, or the like. The rear housing 13 serves as a protective structure disposed at the back of the electronic device 100, and is used to carry and protect internal components of the electronic device 100. After the back cover 11 and the rear housing 13 are assembled together, the back cover 11 slightly exceeds the rear housing 13, so that the back cover 11 may preferentially contact the skin of the user when the electronic device 100 is worn on the user, thereby facilitating contact between the first ECG electrode 20 and the skin of the user. The rear housing 13 and the middle frame 12 may be assembled by snap-fitting and bonded with each other via adhesive, or directly bonded with each other via adhesive. Alternatively, the rear housing 13 and the middle frame 12 may be stably connected via fixing members such as screws, pins, and rivets. The back cover 11 and the rear housing 13 may be connected by snap-fitting, which facilitates detachment of the back cover 11, so that it is easy to maintain functional components inside the electronic device 100 without disassembling the whole machine. In other implementations, the rear housing 13 may also be integrally pre-formed with the middle frame 12, and a space for plating electrodes is reserved in the rear housing 13, such that the second ECG electrode 30 may be formed in the rear housing 13 through electroplating after the rear housing 13 and the middle frame 12 are integrally formed.

Optionally, the middle frame 12 may be made of metal, so that metal texture requirements of the electronic device 100 can be met.

Optionally, the rear housing 13 may be made of materials such as glass, pottery, sapphire, metal, and plastic, such that requirements of the rear housing 13 such as firmness, wear resistance, scratch resistance, fire prevention, explosion-proof, and dust-proof can be met.

Optionally, the back cover 11 may be made of glass, ceramics, sapphire, and other materials to meet the requirements of firmness, wear resistance, and scratch resistance, and may provide an insulating environment for the first ECG electrode 20 to facilitate a detection of the heart rate of the user by the first ECG electrode 20.

Figure 3:
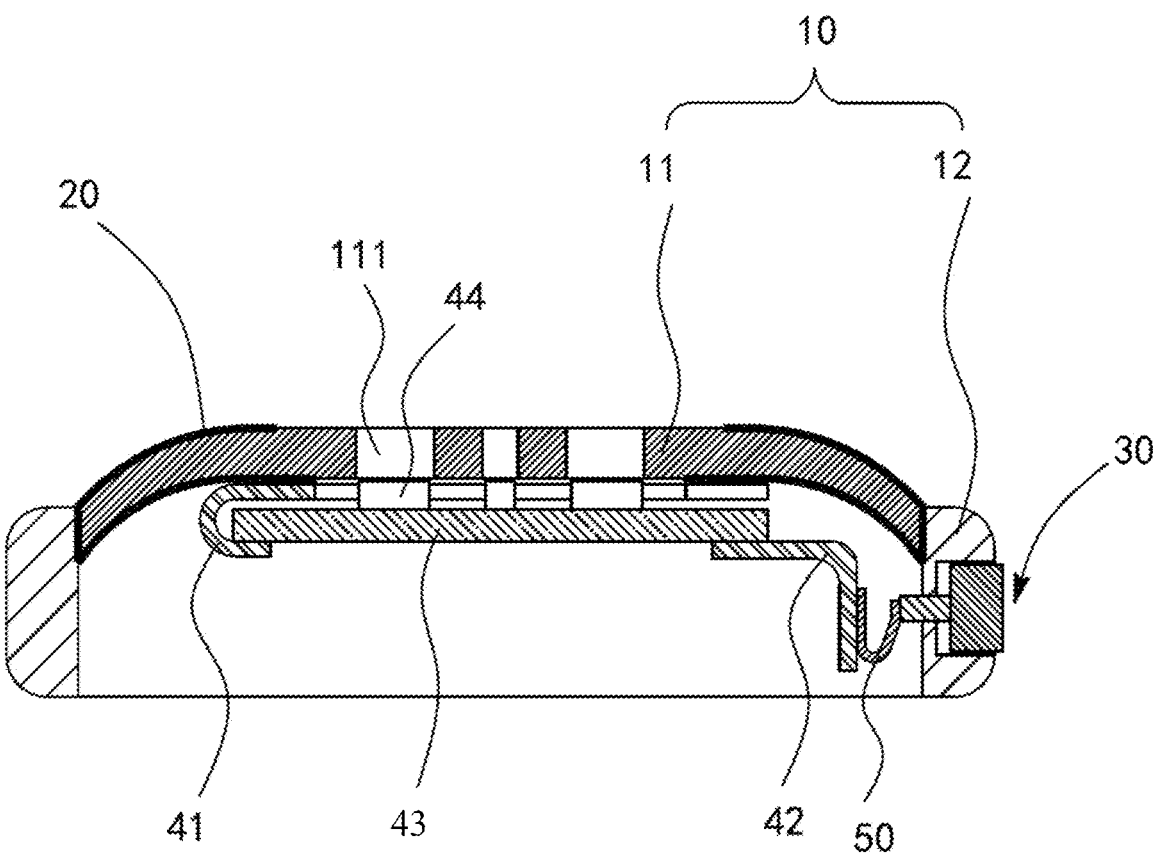
FIG. 3 is a schematic partial cross-sectional view of an electronic device provided in an implementation of the disclosure.
Figure 4:
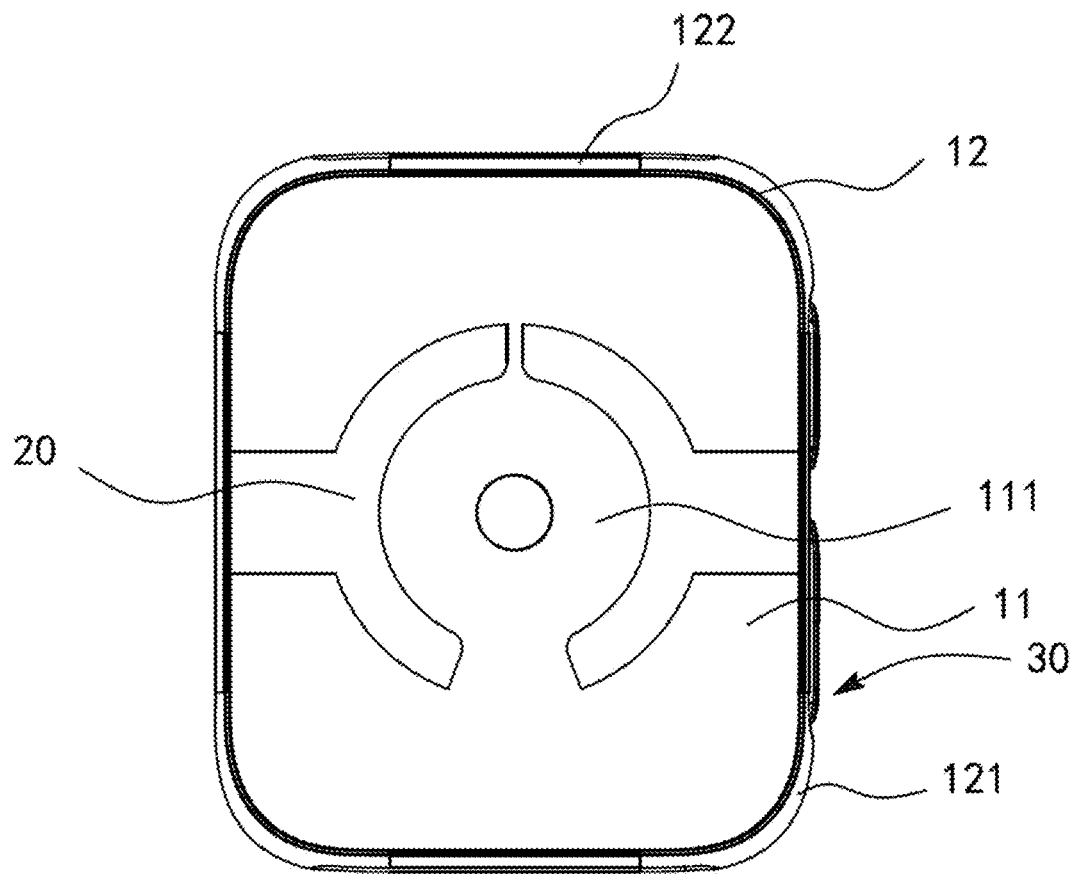
FIG. 4 is a schematic top view of the electronic device provided in the implementation illustrated in FIG. 3 of the disclosure.

In another implementation, as illustrated in FIG. 3 and FIG. 4, a periphery of the back cover 11 is fixedly connected with the middle frame 12, and the back cover 11 serves as a protective structure at the back of the electronic device 100. The back cover 11 carries and protects functional components inside the electronic device 100. The back cover 11 is directly engaged with the middle frame 12, such that a structure of the housing 10 is simplified and an assembly of the housing 10 is easy.

In the implementations, in a case that the back cover 11 is made of sapphire or ceramic, the first ECG electrode 20 is attached to a surface of the back cover 11 and further extends from an edge of the back cover 11 to an inner surface of the back cover 11, so that the first ECG electrode 20 is electrically connected with the first branch 41. The first ECG electrode 20 and the back cover 11 are integrally formed to increase stability of the first ECG electrode 20 relative to the back cover 11. For example, the first ECG electrode 20 may be formed on the back cover 11 through metal plating such as chrome plating, zinc plating, or aluminum plating. The first ECG electrode 20 may be implemented as two first ECG electrodes 20. One of the two first ECG electrodes 20 may be used as a compensation electrode and configured to transmit a compensation signal to the user, so that interference generated by the user can be counteracted to ensure accuracy of the ECG data of the user obtained by the other one of the two first ECG electrodes 20 and the second ECG electrode 30. The other one of the two first ECG electrodes 20 may be used as a detection electrode, and configured to cooperate with the second ECG electrode 30 to form a conductive path with the user, so that an ECG voltage under the skin tissue of the user can be obtained. The two first ECG electrodes 20 are arranged opposite to each other, and each of the two first ECG electrodes 20 is in a substantially semi-annular shape. The two first ECG electrodes 20 are arranged at the periphery of the back cover 11. The two first ECG electrodes 20 cooperatively form a substantially annular electrode. A partition structure is arranged between the two first ECG electrodes 20 so that the two first ECG electrodes 20 are spaced apart from each other. In other implementations, the first ECG electrode 20 may also be a metal part embedded in the back cover 11, or a metal part bonded to the back cover 11.

Figure 5:
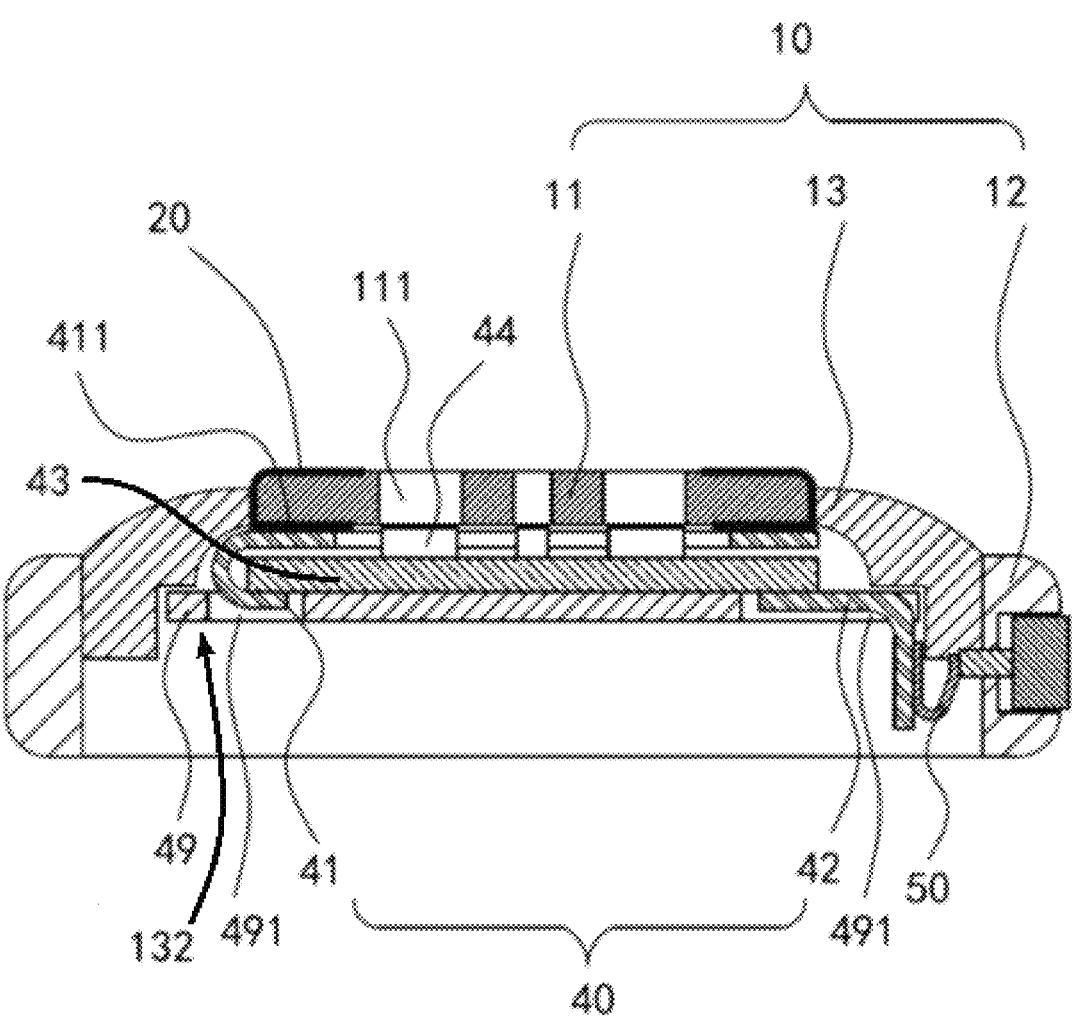
FIG. 5 is a schematic partial cross-sectional view of an electronic device provided in another implementation of the disclosure.

In the implementations, refer to FIG. 1, FIG. 2, and FIG. 5, the first branch 41 extends from an edge of a printed circuit board (PCB) substrate 43 close to the first ECG electrode 20, so that the first branch 41 may be effectively shortened. The first branch 41 is attached to the back cover 11, and the first branch 41 is provided with two soldering regions 411 at an end of the first branch 41 away from the PCB substrate 43. The soldering region 411 is provided with but is not limited to an exposed copper structure, and may also be provided with a metal oxide pad structure, or a silver layer structure. The exposed copper structure of the soldering region 411 may be soldered with part of the first ECG electrode 20 extending to the inner surface of the back cover 11, so that a conduction between the first branch 41 and the two first ECG electrode 20 can be achieved, that is, the first branch 41 is in electrical connection with the two first ECG electrode 20. The first branch 41 is provided with conductive lines in conduction with the two first ECG electrodes 20. The first branch 41 is used to conduct electrical signals of the first ECG electrode 20 to the PCB substrate 43 of the ECG circuit board 40. The first branch 41 is attached to the back cover 11, so that a thickness of a stacking of the first branch 41 and the back cover 11 can be reduced, thereby reducing a thickness of the electronic device 100. The first branch 41 may be a flexible printed circuit board (FPCB), so that the first branch 41 can be bent relative to the PCB substrate 43, thereby facilitating an electrical connection between the first branch 41 and the first ECG electrode 20, and effectively reducing a space occupied by the first branch 41. The first branch 41 and the PCB substrate 43 may be fixed by soldering, or by a rigid-flex way. The first branch 41 may be bent relative to and stacked on the PCB substrate 43, so that an internal structure of the electronic device 100 can be relatively compact and an internal space arrangement of the electronic device 100 can be optimized. The first branch 41 is in a substantially annular shape, so that the first branch 41 may be disposed around electronic components on the ECG circuit board 40 to prevent signals of the first branch 41 from being interfered by the electronic components on the ECG circuit board 40. In other implementations, the first branch 41 may also be bonded to the back cover 11 via conductive adhesive, and be in conduction with the first ECG electrode 20.

In the implementations, the ECG circuit board 40 is provided with the PCB substrate 43 and a photoplethysmograph (PPG) 44 disposed on the PCB substrate 43. The PCB substrate 43 is fixed inside the middle frame 12 and spaced apart from the back cover 11. The back cover 11 is provided with multiple light-transmitting portions 111 corresponding to the photoplethysmograph 44. Part of the light-transmitting portions 111 is used for outgoing of light rays from the photoplethysmograph 44, and the rest of the light-transmitting portions is used for incidence of light rays reflected by the skin tissue of the user. The first ECG electrode 20 is disposed around the multiple light-transmitting portions 111, so that the back cover 11 can be sufficiently utilized. In the electronic device 100, the first ECG electrode 20 and the second ECG electrode 30 may serve as the ECG components, and be used to obtain ECG data in combination with the photoplethysmograph 44. It may be understood that other components are also provided on the ECG circuit board 40 to meet other functional requirements of the electronic device 100.

In the implementations, the second branch 42 extends from an edge of the PCB substrate 43 close to one of the first sides 122, and the second ECG electrode 30 is disposed on the one of the first sides 122, so that the second branch 42 may be effectively shortened, thereby effectively shortening a closed conduction path between the ECG circuit board 40 and the second ECG electrode 30, and in turn effectively shortening a closed conduction path between the first ECG electrode 20 and the second ECG electrode 30. The second branch 42 may be a flexible circuit board (FPC), facilitating an electrical connection between the second branch 42 and the second ECG electrode 30 and reducing a space occupied by the second branch 42. The second branch 42 and the PCB substrate 43 may be fixed by soldering, or by a rigid-flex way. The second branch 42 may be bent relative to the PCB substrate 43, so that an end of the second branch 42 away from the PCB substrate 43 may be stacked with the second ECG electrode 30 in a direction substantially perpendicular to the PCB substrate 43, thereby avoiding that the second branch 42 is stacked with the second ECG electrode 30 in a direction parallel to the PCB substrate 43, and thus the thickness of the electronic device 100 is further optimized and reduced, internal structure arrangement of the electronic device 100 is relatively compact, and usage of internal space of the electronic device 100 is optimized. The end of the second branch 42 away from the PCB substrate 43 is provided with but is not limited to an exposed copper structure, and may also be provided with a metal oxide pad structure, or a silver layer structure. A conduction between the second branch 42 and the conductive resilient sheet 50 is achieved via the exposed copper structure, so that a conduction between the second ECG electrode 30 and the first ECG electrode 20 can be achieved via the conductive resilient sheet 50, the second branch 42, the PCB substrate 43, and the first branch 41. It may be understood that, since the first branch 41 and the second branch 42 directly extend from the PCB substrate 43 and have simple structures, the first branch 41 and the second branch 42 can be effectively shortened, and the closed conduction path between the first ECG electrode 20 and the second ECG electrode 30 are effectively shortened. As such, when the second ECG electrode 30 is touched by the user, electric signals from the user may be quickly transmitted to the first ECG electrode 20 via the second branch 42, the PCB substrate 43, and first branch 41, and a sensitivity of obtaining the ECG data of the user by the electronic device 100 can be improved.

In the implementations, the conductive resilient sheet 50 is in contact with the second branch 42, so that a conduction between the conductive resilient sheet 50 and the second branch 42 can be achieved. The conductive resilient sheet 50 may be in direct contact with the second ECG electrode 30, or the conduction between the conductive resilient sheet 50 and the second ECG electrode 30 may be realized via a conductive member. The conduction between the second ECG electrode 30 and the second branch 42 is realized via the conductive resilient sheet 50, so that it is convenient to assemble the ECG circuit board 40 and the second branch 42 with the middle frame 12 and the second ECG electrode 30, simplifying a conductive structure between the second branch 42 and the second ECG electrode 30, and avoiding an excessively complicated conduction structure between the second ECG electrode 30 and the second branch 42. The conductive resilient sheet 50 may be fixed on the middle frame 12 or other fixing members inside the middle frame 12, and resiliently contact the second branch 42 and the second ECG electrode 30. The conductive resilient sheet 50 may also be fixed on the second branch 42 and resiliently contact the second ECG electrode 30, or may be fixed on the second ECG electrode 30 and resiliently contact the second branch 42.

Figure 6:
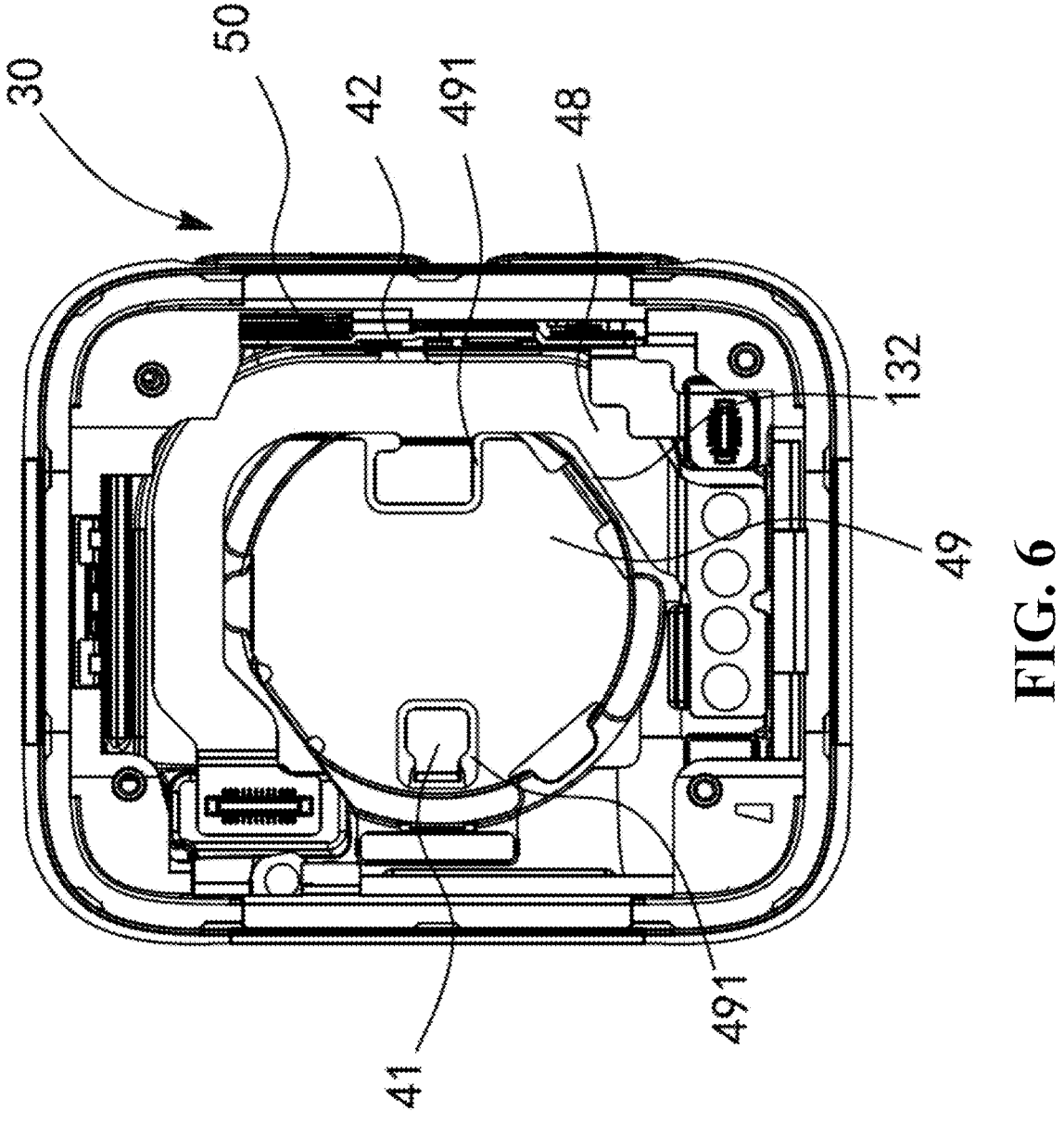
FIG. 6 is a schematic internal structural view of the electronic device provided in the implementation illustrated in FIG. 5 of the disclosure.

In the implementations, as illustrated in FIG. 5 and FIG. 6, the electronic device 100 further includes a pressing cover plate 49 fixed inside the rear housing 13 and covering the ECG circuit board 40. The pressing cover plate 49 is fixed with the rear housing 13 by a pressing way, so that the ECG circuit board 40 is stably fixed between the pressing cover plate 49 and the rear housing 13, facilitating a stable connection of the ECG circuit board 40 relative to the rear housing 13, and an effective conduction among the ECG circuit board 40, the first ECG electrode 20, and the second ECG electrode 30.

Specifically, the rear housing 13 defines a recess 132 on an inner side thereof, and the ECG circuit board 40 is fixed in the recess 132. The first branch 41 is located between the PCB substrate 43 and the rear housing 13, so that the first branch 41 may stably contact the first ECG electrode 20. The pressing cover plate 49 may be engaged with the rear housing 13 at an opening end of the recess 132 by snap-fitting, so that the pressing cover plate 49 can be detachable, thereby facilitating detachment and maintenance of the ECG circuit board 40. More specifically, the pressing cover plate 49 defines two through grooves 491, and the two through grooves 491 match a portion of the first branch 41 connected with the PCB substrate 43 and a portion of the second branch 42 connected with the PCB substrate 43, respectively, preventing the first branch 41 and the second branch 42 from being crushed by the pressing cover plate 49. The through groove 491 matching the second branch 42 defines an opening on an edge of the pressing cover plate 49, so that the second branch 42 can extend out of the opening of the through groove 491, thereby facilitating the conduction between the second branch 42 and the conductive resilient sheet 50.

Further, in the implementations, the rear housing 13 further defines a charging port 133 (see FIG. 2). The ECG circuit board 40 is further provided with a conductive branch 48 communicating with the charging port 133, and the charging port 133 is adjacent to the second side 122. The conductive branch 48 is disposed around a peripheral side of the ECG circuit board 40. The conductive branch 48 extends from an end of the second branch 42 connected with the ECG circuit board 40. An end of the conductive branch 48 away from the charging port 133 may be connected with a main board of the electronic device 100 via a board-to-board connector, so that the main board of the electronic device 100 can control the charging port 133 to obtain power from an external power source, thereby facilitating charging a battery through the charging port 133 and the conductive branch 48, and supplying power to the ECG circuit board 40, the first branch 41, and the second branch 42 by the battery.

Figure 7:
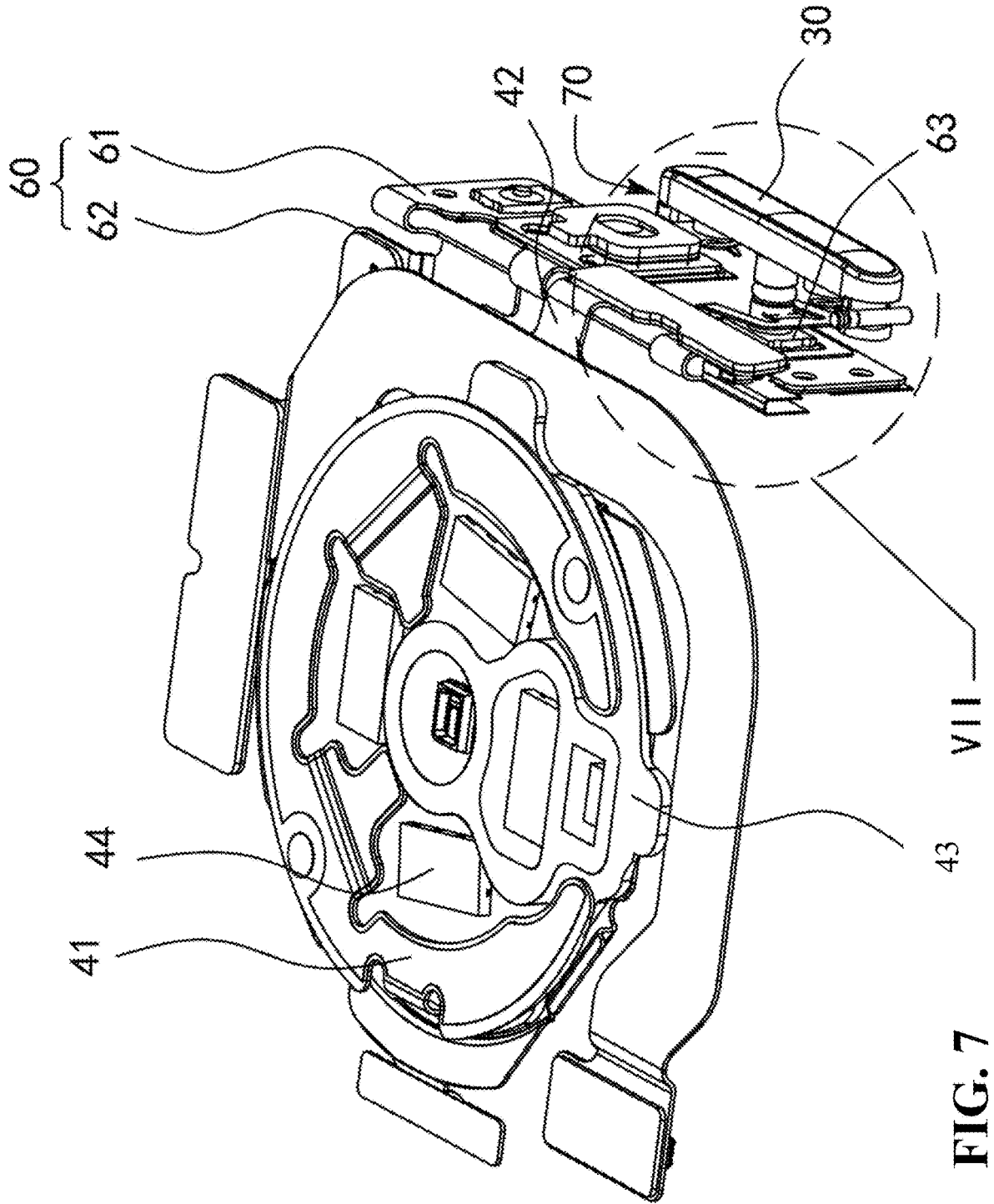
FIG. 7 is a schematic partial perspective view of an electronic device provided in an implementation of the disclosure.
Figure 8:
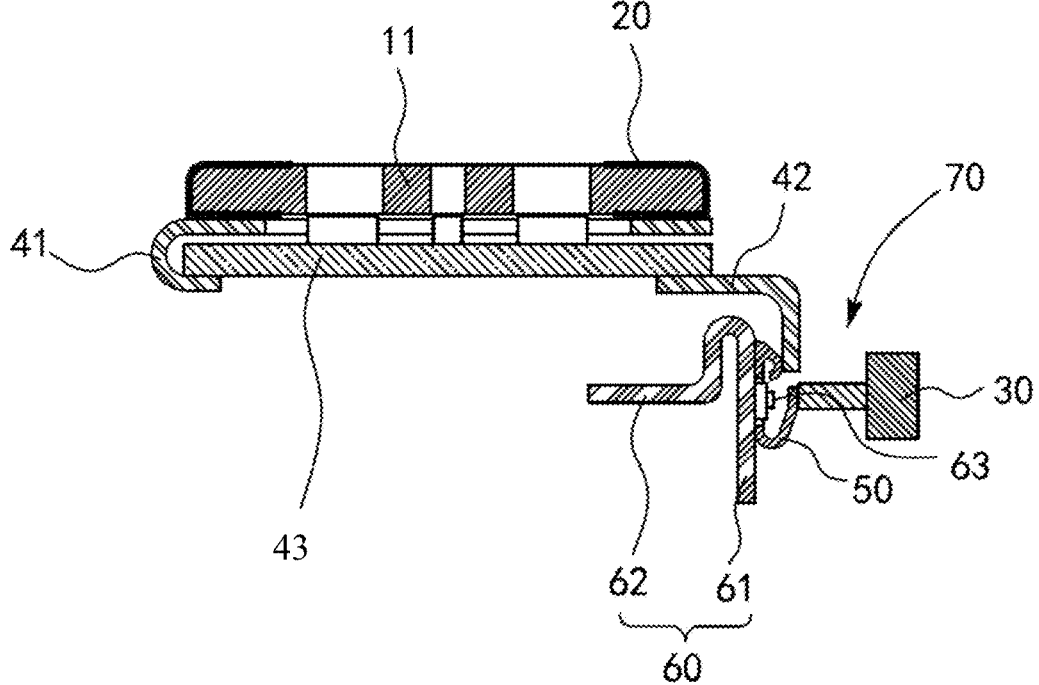
FIG. 8 is a schematic partial cross-sectional view of an electronic device provided in another implementation of the disclosure.
Figure 9:
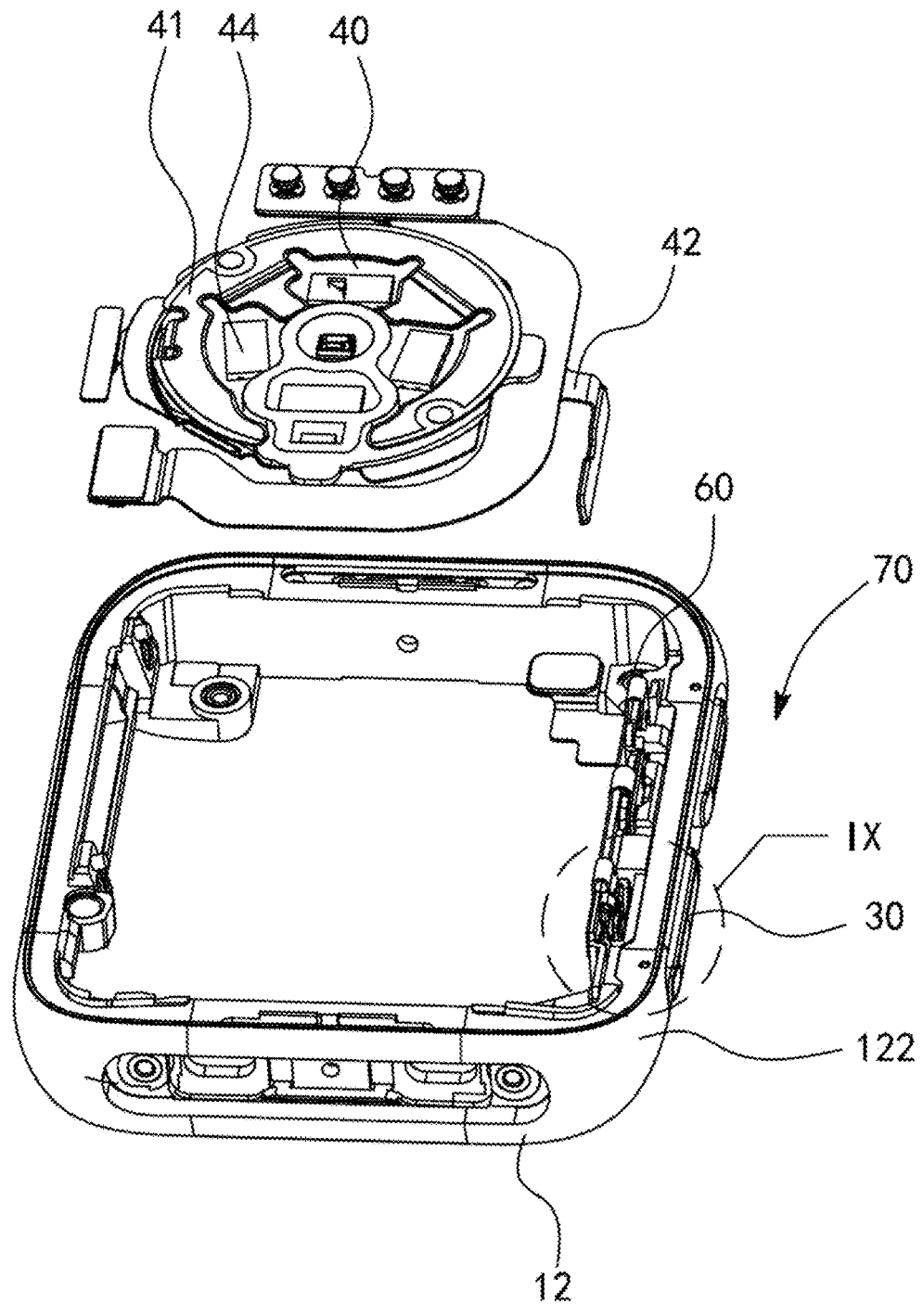
FIG. 9 is a schematic partial exploded view of an electronic device provided in an implementation of the disclosure.

In an implementation, refer to FIG. 7, FIG. 8, and FIG. 9, an example that the conductive resilient sheet 50 is disposed on a side-button circuit board 60 that is stably fixed inside the middle frame 12 is taken for illustration. In the implementation, the electronic device 100 further includes the side-button circuit board 60 fixed inside the middle frame 12, and the conductive resilient sheet 50 is fixedly connected with the side-button circuit board 60. The side-button circuit board 60 has a first portion 61 spaced apart from an inner wall of the first side 121 and a second portion 62 bent relative to the first portion 61 and connected to the ECG circuit board 40. An end of the second portion 62 away from the first portion 61 may be connected to the main board of the electronic device 100 via a board-to-board connector, so that a signal of a button switch 63 can be transmitted to the main board of the electronic device 100. A strength of the first portion 61 is greater than that of the second portion 62, so that the conductive resilient sheet 50 can be fixed on the first portion 61, and the first portion 61 can be provided with the button switch 63 that can be readily triggered by a side button 70. A gap is defined between the first portion 61 and the inner wall of the middle frame 12, and the end of the second branch 42 away from the PCB substrate 43 is stacked in the gap between the first portion 61 and the inner wall of the middle frame 12, so that an assembly of the side-button circuit board 60 and the middle frame 12 can be relatively compact in structure, the internal space arrangement of the electronic device 100 can be optimized, and the conductive resilient sheet 50 can be closer to the second ECG electrode 30 in the middle frame 12. It may be understood that, the first portion 61 may be provided with a reinforcing layer, so that the strength of the first portion 61 may be greater than that of the second portion 62. The side-button circuit board 60 may also be configured as a rigid-flex circuit board, so that the strength of the first portion 61 is greater than that of the second portion 62. The second portion 62 may be freely bent, facilitating a connection between the second portion 62 and the main board of the electronic device 100, and thus facilitating transmission of the signal of the button switch 63 on the side-button circuit board 60 to the main board of the electronic device 100.

In the implementations, the electronic device 100 further includes a side button 70 connected with the middle frame 12, where the side button 70 can be pressed. The side-button circuit board 60 is provided with the button switch 63 corresponding to the side button 70. The button switch 63 is disposed on a side surface of the first portion 61 close to the inner wall of the middle frame 12, so that the side button 70 can trigger the button switch 63. The second ECG electrode 30 is disposed at the side button 70, so that an electrical signal can be transmitted to the first ECG electrode 20 via the second ECG electrode 30 when the side button 70 is touched by the user, and the ECG data can be obtained by the electronic device 100. The side button 70 may also be pressed by the user to realize a control of the electronic device 100, thereby optimizing an arrangement of components on the middle frame 12.

Specifically, the electronic device 100 is provided with two side buttons 70 arranged side by side on the first side 121. The second ECG electrode 30 is disposed at one of the two side buttons 70. The side-button circuit board 60 is provided with two button switches 63 respectively corresponding to the side buttons 70 on both sides of the side-button circuit board 60, and the two side buttons 70 may respectively trigger the two button switches 63 to send signals. The conductive resilient sheet 50 is adjacent to one of the two button switches 63 that faces the side button 70 where the second ECG electrode 30 is located. It may be understood that, with aid of the side button 70 provided with the second ECG electrode 30, it is possible to realize a control function of the electronic device 100, and furthermore, when the side button 70 is touched by the user, the second ECG electrode 30 can also be touched, and thus the electronic device 100 can obtain the ECG data of the user. The other one of the two side buttons 70 can be used to realize a control function of the electronic device 100 different from the control function of the electronic device 100 realized with aid of the side button 70 provided with the second ECG electrode 30, so that the electronic device 100 has various control functions.

Figure 10:
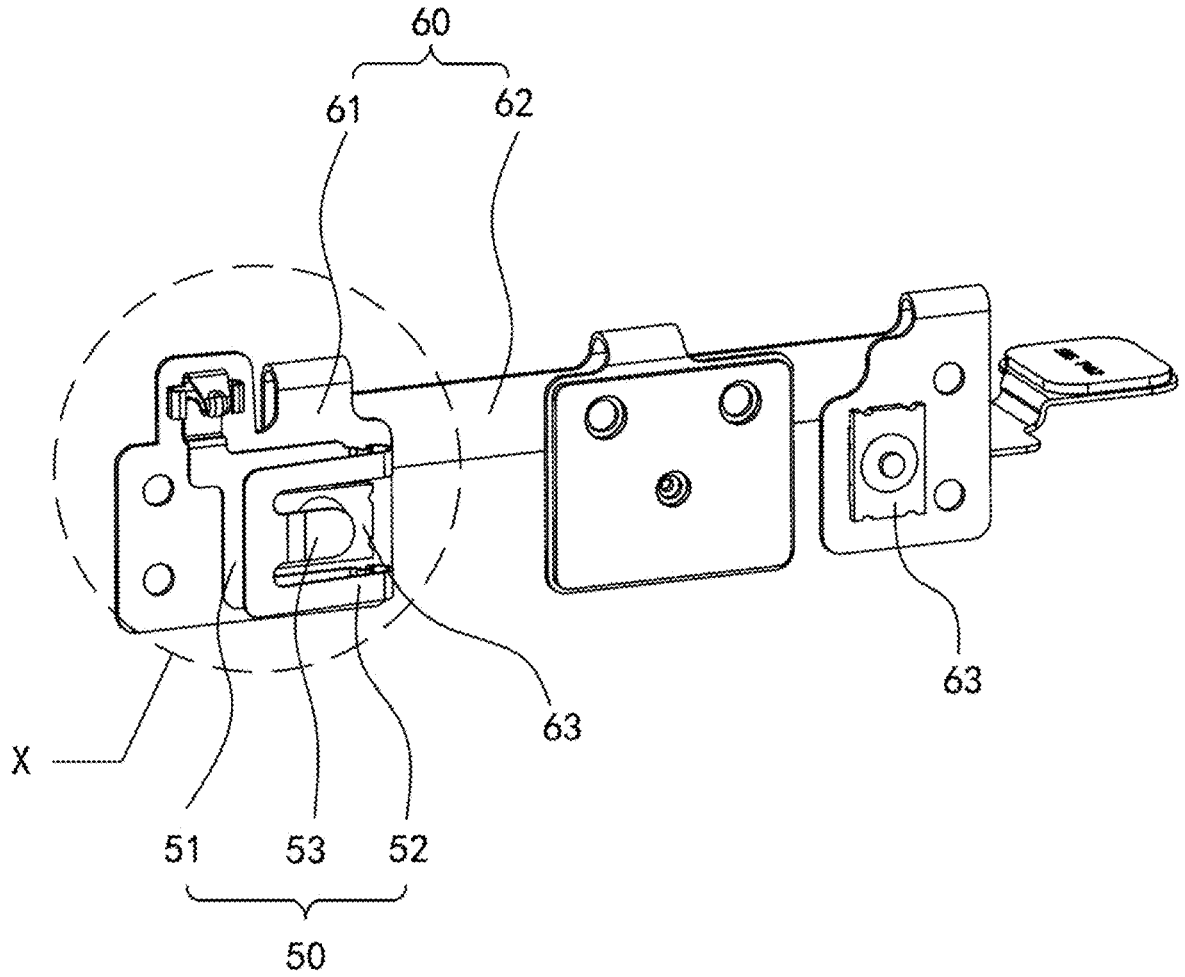
FIG. 10 is a schematic partial perspective view of electronic device provided in another implementation of the disclosure.

Further, in an implementation, refer to FIG. 10, the conductive resilient sheet 50 is provided with a fixed base 51 and a resilient arm 52, where the fixed base 51 is close to the button switch 63 and attached to the side-button circuit board 60, and the resilient arm 52 extends from the fixed base 51 in a bent way. An end portion of the resilient arm 52 faces the button switch 63 and resiliently abuts against the side button 70. The fixed base 51 is provided with a U-shaped ring at a peripheral side of the button switch 63, and the resilient arm 52 extends from two free ends of the U-shaped ring and is bent relative to the U-shaped ring. The resilient arm 52 is also in the shape of a U-shaped ring. The resilient arm 52 is provided with a resilient tab 53 at a closed end of the resilient arm 52, and the resilient tab 53 extends toward an open end of the U-shaped ring. An end of the resilient tab 53 faces the button switch 63, and the resilient tab 53 resiliently abuts against the side button 70, so that a conduction between the resilient arm 52 and the second ECG electrode 30 can be achieved. The fixed base 51 is located at the peripheral side of the button switch 63, so that the resilient arm 52 can resiliently resist against the side button 70 effectively, and an effective conduction between the second ECG electrode 30 and the conductive resilient sheet 50 can be achieved. The fixed base 51 is spaced apart from the button switch 63, avoiding a short circuit between the conductive resilient sheet 50 and the button switch 63, and preventing a trigger signal of the button switch 63 from interfering with conduction of an electrical signal of the second ECG electrode 30 by the conductive resilient sheet 50.

Optionally, the fixed base 51 may be fixedly connected with the side-button circuit board 60 via insulating adhesive, to avoid a short circuit between the side-button circuit board 60 and the conductive resilient sheet 50.

Optionally, the conductive resilient sheet 50 may be a metal piece containing silver, magnesium, aluminum, copper, or the like.

It may be appreciated that, a conductive line connected to the button switch 63 on the side-button circuit board 60 is routed between the two free ends of the U-shaped ring of the fixed base 51, so that the conductive line connected to the button switch 63 can be kept away from the fixed base 51, the conduction of the electrical signal of the second ECG electrode 30 via the conductive resilient sheet 50 can be independent of a conduction of an electrical signal of the button switch 63, and thus the accuracy of the ECG data obtained and a control accuracy of the side button 70 can be ensured.

During obtaining of the ECG data of the user by the second ECG electrode 30, the first ECG electrode 20 is in contact with the skin of the wrist of the user, and when the side button 70 provided with the second ECG electrode 30 is touched and pressed by the user or is merely touched by the user, a closed conduction path is formed among the second ECG electrode 30, the conductive resilient sheet 50, the second branch 42, the PCB substrate 43, the first branch 41, the first ECG electrode 20, and the user. Further, the first ECG electrode 20 and the second ECG electrode 30 contacts two non-equipotential portions of the user, respectively, so that a potential difference is formed between the second ECG electrode 30 and the first ECG electrode 20, and thus the ECG data of the user can be obtained by the electronic device 100 with aid of the components on the ECG circuit board 40.

During triggering of the button switch 63 by the side button 70, the side button 70 is pressed by the user, and then the side button 70 drives the resilient tab 53 and the resilient arm 52 to deform to make the resilient tab 53 abut against the button switch 63, and thus the button switch 63 sends signal, that is, the button switch 63 is eventually triggered.

Figure 11:
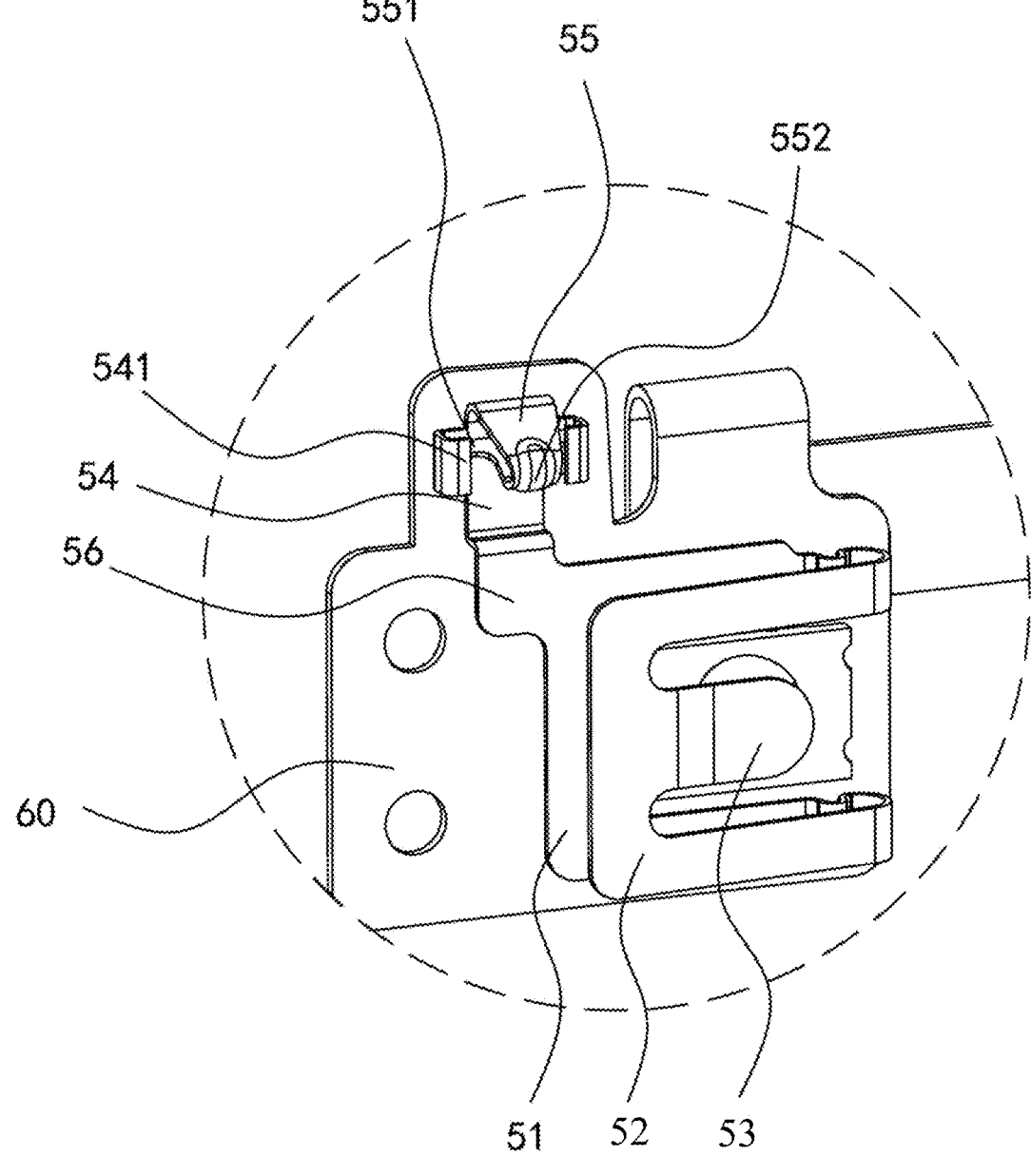
FIG. 11 is a schematic enlarged view of the electronic device at circle X in FIG. 10.
Figure 12:
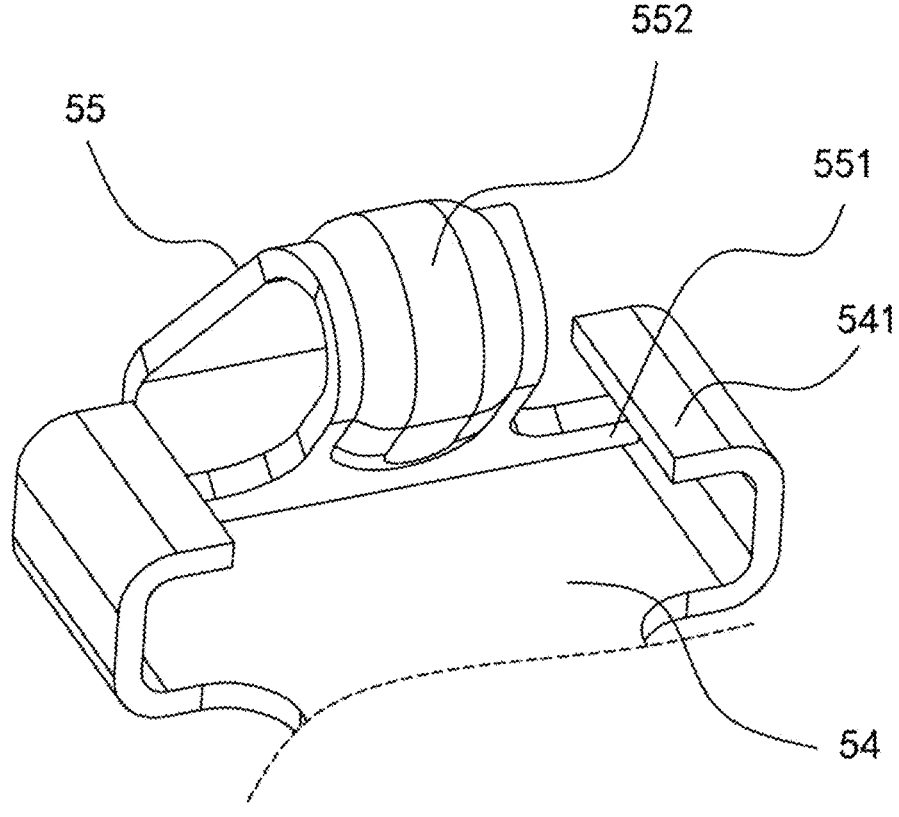
FIG. 12 is a schematic enlarged view of a branch base and a branch resilient arm in the implementation illustrated in FIG. 10 of the disclosure.
Figure 13:
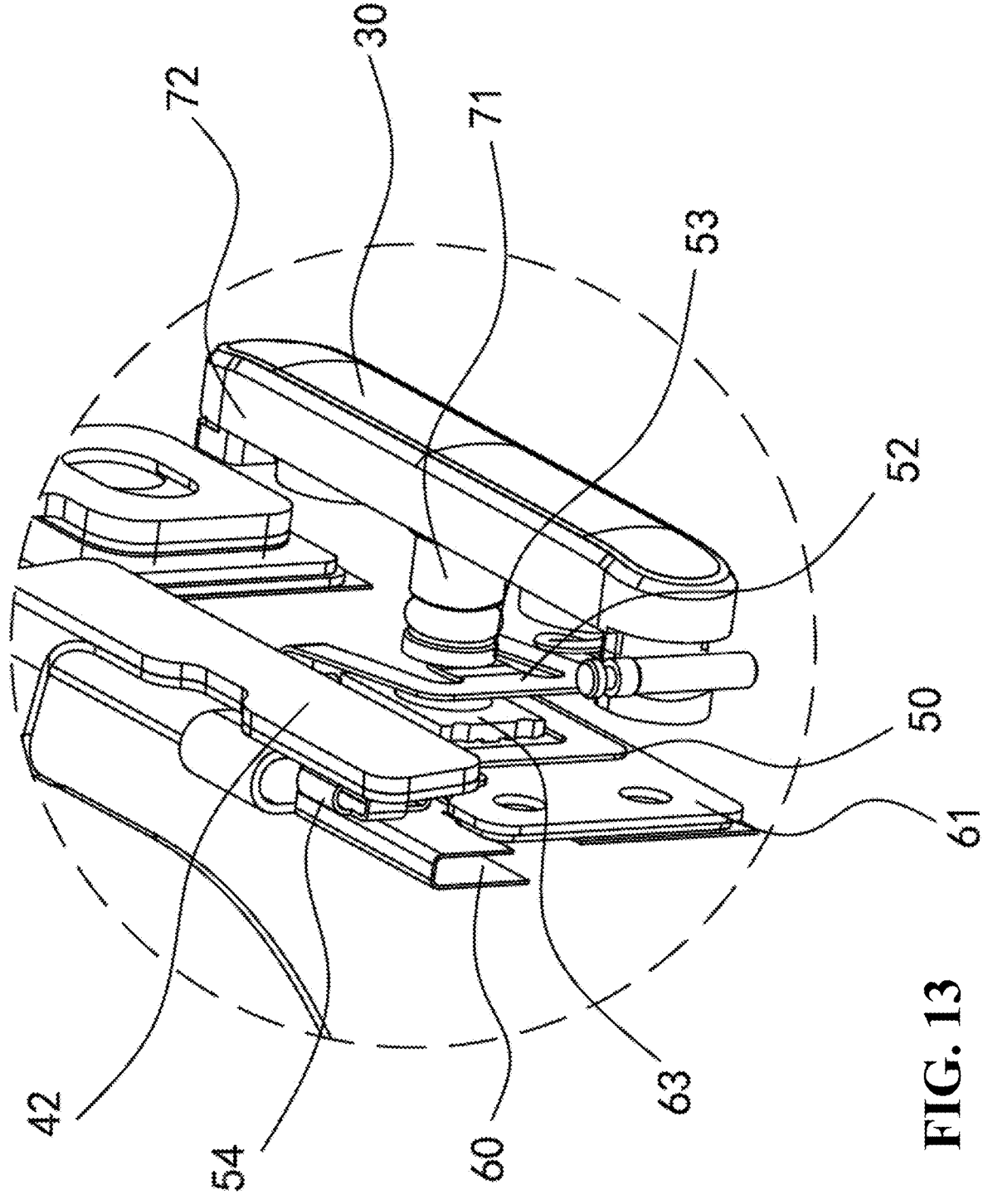
FIG. 13 is a schematic enlarged view of the electronic device at circle VII in FIG. 7.
Figure 14:
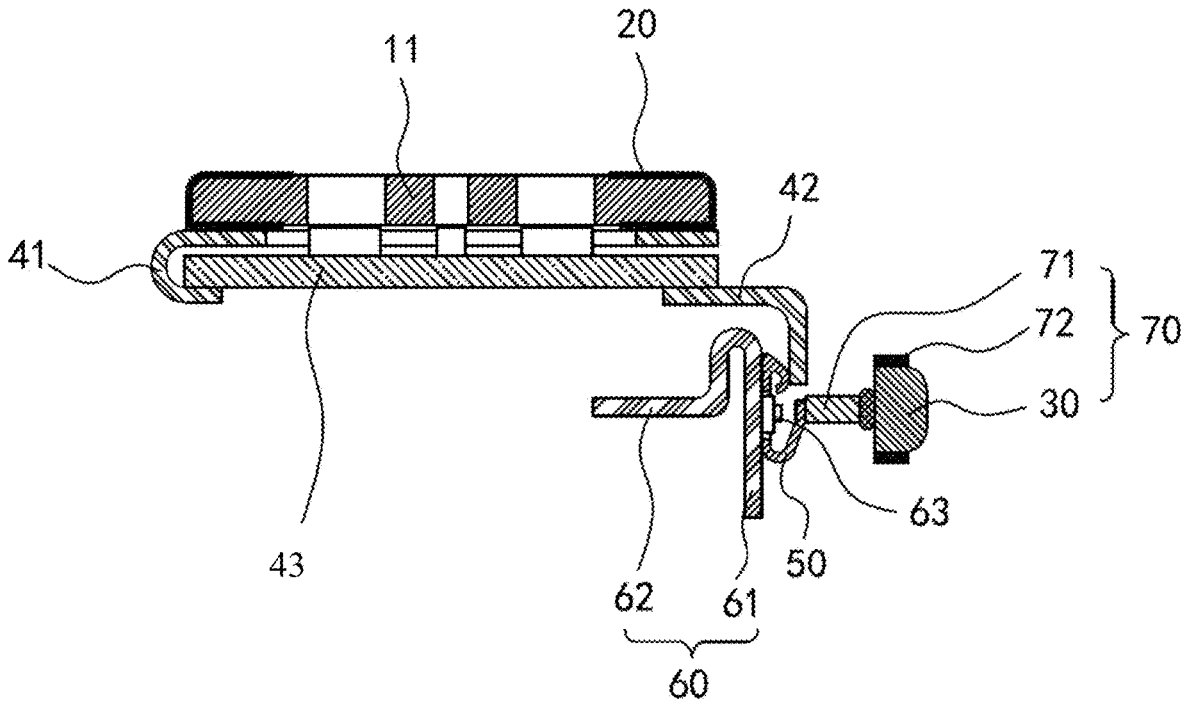
FIG. 14 is a schematic partial cross-sectional view of an electronic device provided in another implementation of the disclosure.

In an implementation, refer to FIG. 10 and FIG. 11, the conductive resilient sheet 50 is further provided with a branch base 54 extending from the fixed base 51 and a branch resilient arm 55 extending from the branch base 54 in a bent way, the branch base 54 is attached to the side-button circuit board 60, and the branch resilient arm 55 resiliently abuts against the second branch 42. The branch base 54 extends from an closed end of the U-shaped ring of the fixed base 51, so that a stability of the branch base 54 relative to the fixed base 51 can be increased. The branch base 54 is located on the side-button circuit board 60 at a position close to the back cover 11, so that the branch base 54 is close to the second branch 42, and thus a path from the first ECG electrode 20 to the conductive resilient sheet 50 is shortened. An extension arm 56 is connected between the branch base 54 and the fixed base 51, and the extension arm 56 is attached to the side-button circuit board 60, so that the conductive resilient sheet 50 as a whole is stably fixed with the side-button circuit board 60. The branch resilient arm 55 extends from an edge of the branch base 54 away from the extension arm 56, so that the branch resilient arm 55 is inclined relative to the side-button circuit board 60, facilitating a resilient abutting of the branch resilient arm 55 against the second branch 42.

During assembly of the second branch 42 with the side-button circuit board 60, the second branch 42 may first contact the branch resilient arm 55 and eventually resiliently contact an end of the branch resilient arm 55, so that the end of the branch resilient arm 55 can be prevented from puncturing by the second branch 42. The branch base 54 extends from the fixed base 51, and the branch resilient arm 55 extends from the branch base 54, so that the branch resilient arm 55, the branch base 54, the fixed base 51, and the resilient arm 52 are integrally formed, facilitating an effective conduction between the second branch 42 and the second ECG electrode 30 via the conductive resilient sheet 50, and the sensitivity of obtaining the ECG data of the user by the electronic device 100 can be improved.

In order to increase a resilient resistance force of the branch resilient arm 55 against the second branch 42 and prevent the branch resilient arm 55 from puncturing the second branch 42, the branch resilient arm 55 is bent. After the branch resilient arm 55 is bent, the end of the branch resilient arm 55 is bent inwardly toward the branch base 54, so that a resilient stress of the branch resilient arm 55 increases. The branch resilient arm 55 is provided with a bending resistance portion 552 that abuts against the second branch 42. A surface of the bending resistance portion 552 that contacts the second branch 42 is curved, so that stress concentration on the second branch 42 can be reduced, and the second branch 42 can be prevented from being punctured.

In order to facilitate an effective resilient abutment between the branch resilient arm 55 and the second branch 42 and ensure an effective resilience of the branch resilient arm 55, the branch base 54 is provided with two limit buckles 541 opposite each other, and the two limit buckles 541 may effectively limit an end of the branch resilient arm 55. Specifically, the two limit buckles 541 respectively extend from the branch base 54 at both sides of the branch resilient arm 55 in a curl and bent way. The two limit buckles 541 are bent relative to the branch base 54, and a limit guide groove is defined between ends of the two limit buckles 541 and the branch base 54.

It is understood that, when being pressed, the branch resilient arm 55 is easy to generate resilient deformation. However, due to that a thickness of the branch resilient arm 55 is generally small, the branch resilient arm 55 is also prone to generate plastic deformation under a force and cannot generate a resilience force to restore to an original state of the branch resilient arm 55. The branch resilient arm 55 is provided with a limit protrusion 551 at an end of the branch resilient arm 55, and the limit protrusion 551 extends into the limit guide groove defined by the two limit buckles 541 and the branch base 54, so that the limit protrusion 551 may be hooked by the two limit buckles 541, and thus the limit protrusion 551 can be effectively limited. When the bending resistance portion 552 is pulled to deform to a large extent, the bending resistance portion 552 drives the limit protrusion 551 to move, and the limit protrusion 551 may then be hooked by the two limit buckles 541, such that the plastic deformation of the branch resilient arm 55 caused by a further pulling and deformation of the bending resistance portion 552 can be avoided. For example, the bending resistance portion 552 can be pulled to increase a distance between the limit protrusion 551 and the branch base 54, and when the distance increases to a certain extent, the limit protrusion 551 will abut against the limit buckles 541 to avoid further increment of the distance, thereby preventing the bending resistance portion 552 from being further pulled.

In an implementation, refer to FIGS. 11-14, the second ECG electrode 30 is disposed at a button cap of the side button 70, the side button 70 is further provided with a button column 71 fixedly connected with the second ECG electrode 30, the button column 71 and the second ECG electrode 30 are in a conducting state, and the button column 71 resiliently abuts against the end portion of the resilient arm 52 and is configured to trigger the button switch 63 when the second ECG electrode 30 is pressed.

It may be understood that the second ECG electrode 30 may be a metal plate, so that the entire button cap of the side button 70 may serve as the second ECG electrode 30. The second ECG electrode 30 may also be a metal layer or a metal sheet formed on a surface of the button cap of the side button 70, that is, part of the surface of the button cap of the side button 70 serves as the second ECG electrode 30. When the entire button cap of the side button 70 serves as the second ECG electrode 30, the side button 70 is also provided with an insulating sleeve 72 sleeved on a periphery side of the second ECG electrode 30. The insulating sleeve 72 is made from an insulating material, so that the insulating sleeve 72 is insulated from the second ECG electrode 30. The second ECG electrode 30 is insulated from the middle frame 12 via the insulating sleeve 72, preventing the middle frame 12 from interfering with reception of electrical signals by the second ECG electrode 30. The button column 71 is a conductive metal member. The button column 71 may be bonded to the second ECG electrode 30 via conductive adhesive. The conductive adhesive can make the second ECG electrode 30 and the button column 71 be in a conducting state. An end of the button column 71 away from the second ECG electrode 30 elastically resists against the resilient tab 53 to achieve a conduction between the conductive resilient sheet 50 and the second ECG electrode 30 via the button column 71. The conductive adhesive has a certain elastic deformation property, so that when the side button 70 tilts up, the conductive adhesive deforms to make the button column 71 not incline, ensuring that the button column 71 can effectively trigger the button switch 63. In order to ensure a waterproof performance of the electronic device 100, a sealing ring is sleeved on a peripheral side of the button column 71, and the sealing ring is sealed against the inner wall of the button hole of the middle frame 12, so that the button hole of the middle frame 12 is sealed to ensure the water resistance of the electronic device 100.

Figure 15:
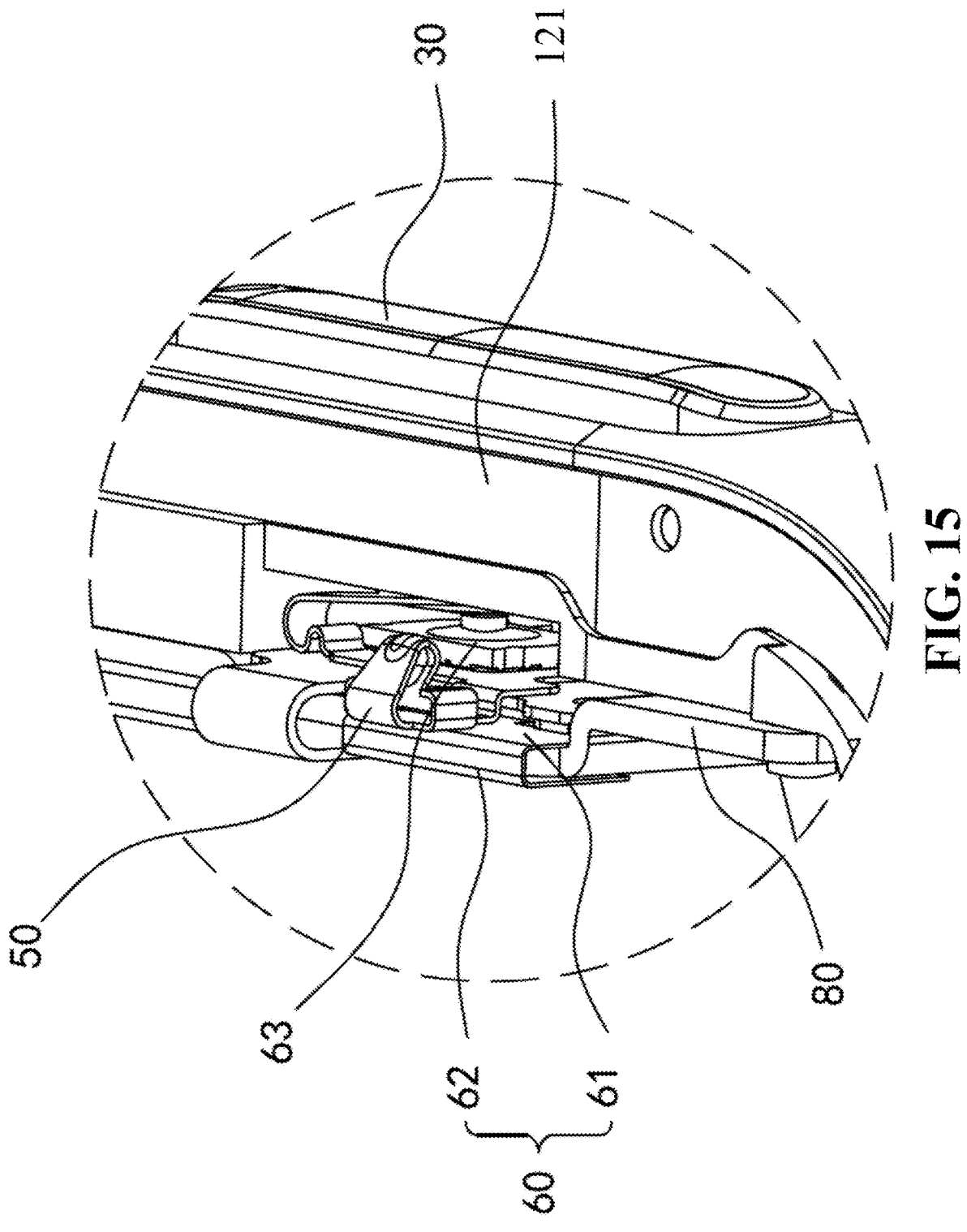
FIG. 15 is a schematic enlarged view of the electronic device at circle IX in FIG. 9.
Figure 16:
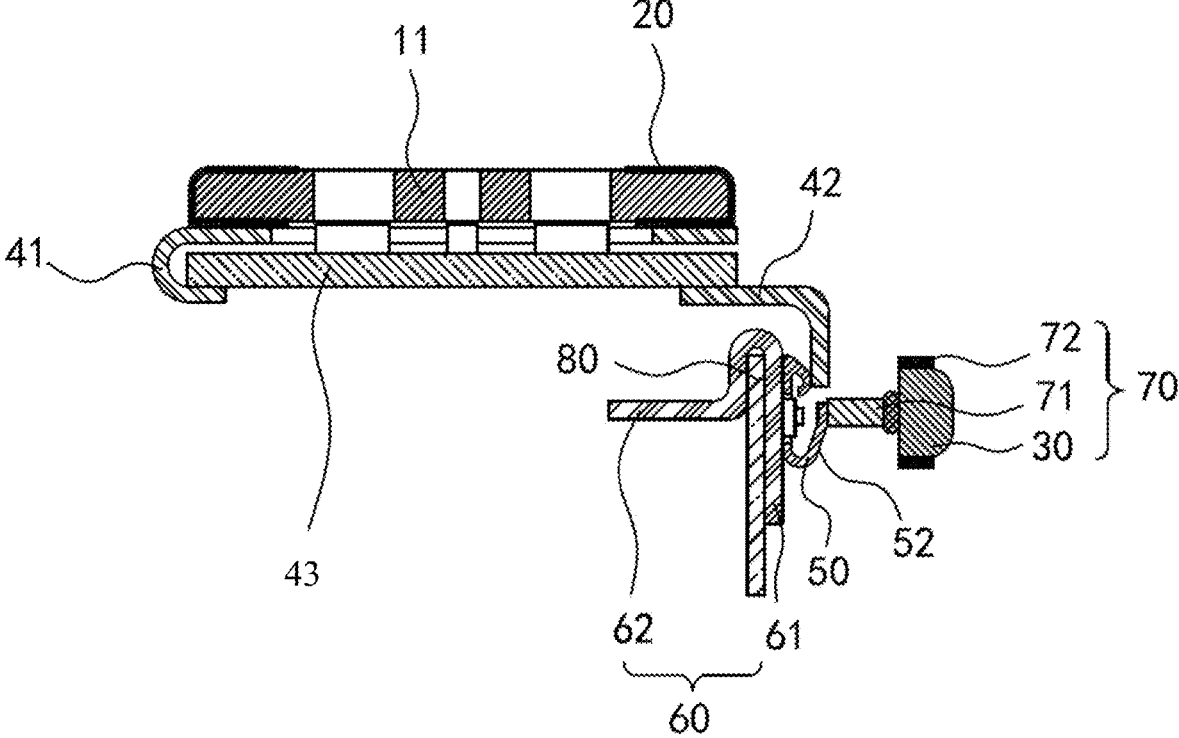
FIG. 16 is a schematic partial cross-sectional view of an electronic device provided in another implementation of the disclosure.

Further, refer to FIG. 15 and FIG. 16, in order to ensure a stability of the second branch 42 relative to the side-button circuit board 60, the electronic device 100 further includes a circuit board support 80. The circuit board support 80 is fixed inside the middle frame 12 and spaced apart from the inner wall of the first side 121. The circuit board support 80 can effectively support the side-button circuit board 60. Specifically, the circuit board support 80 is provided with a plate member spaced apart from the inner wall of the first side 121. The first portion 61 of the side-button circuit board 60 is attached to a side surface of the plate member of the circuit board support 80 close to the second side 122. The second portion 62 of the side-button circuit board 60 is bent relative to the first portion 61 and then attached to a side surface of the plate member of the circuit board support 80 away from the first side 121. In order to facilitate contact between the conductive resilient sheet 50 and the side button 70 and triggering of the button switch 63 by the side button 70, both the conductive resilient sheet 50 and the button switch 63 are disposed on a side surface of the first portion 61 away from the second portion 62 of the side-button circuit board 60, so that the conductive resilient sheet 50 and the button switch 63 may be adjacent to the inner wall of the middle frame 12 and may easily contact the side button 70. In order to facilitate effective contact between the second branch 42 and the conductive resilient sheet 50, the branch base 54 of the conductive resilient sheet 50 is located at an edge of the first portion 61 close to the back cover 11. The end of the second branch 42 away from the PCB substrate 43 is stacked on a side surface of the first portion 61 close to the middle frame 12. The end of the second branch 42 is located within the gap between the side-button circuit board 60 and the middle frame 12, so that the internal space of the electronic device 100 is fully utilized and a structure arrangement is effectively optimized. Apart of the second branch 42 connected with the PCB substrate 43 is bent relative to a part of the second branch 42 stacked on the side-button circuit board 60, and the part of the second branch 42 connected with the PCB substrate 43 extends from an edge of the PCB substrate 43 close to the side-button circuit board 60, so that the second branch 42 can be shortened and the conduction path between the first ECG electrode 20 and the second ECG electrode 30 can be effectively shortened.

Figure 17:
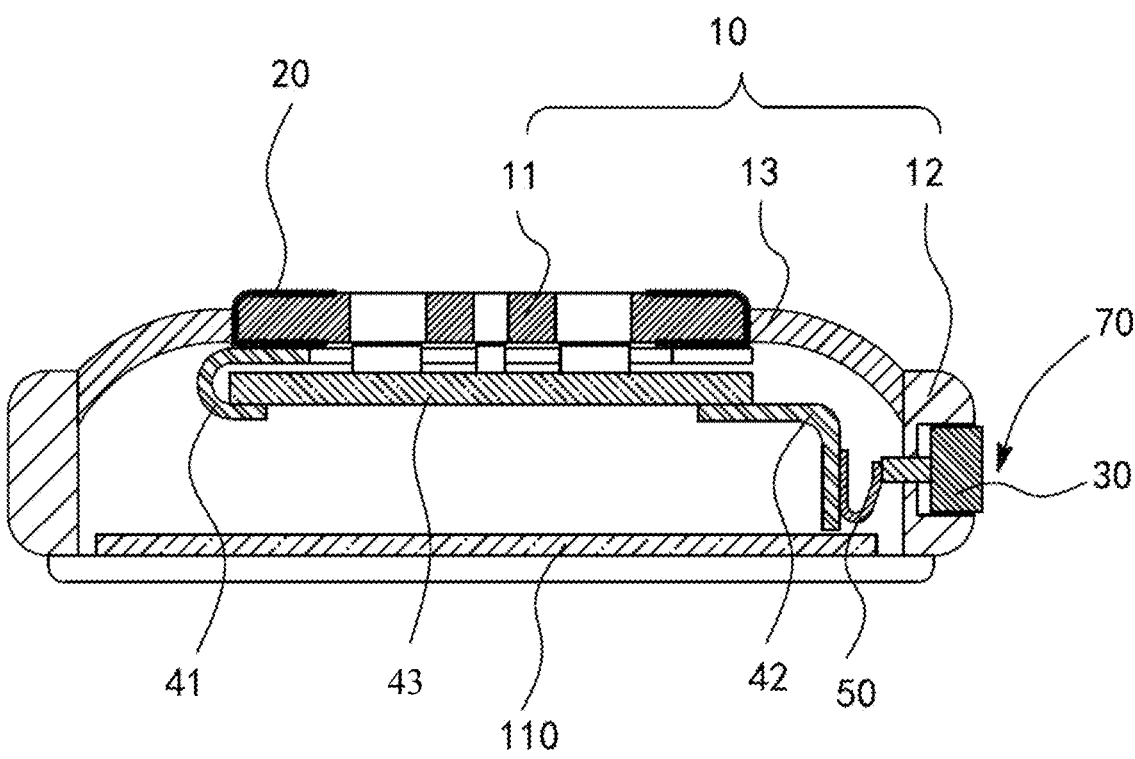
FIG. 17 is a schematic partial cross-sectional view of an electronic device provided in another implementation of the disclosure.

Further, refer to FIG. 17, in order to obtain the ECG data of the user, the electronic device 100 includes a main board and an ECG chip disposed on the main board. The main board may be electrically connected with the ECG circuit board via a flexible circuit board and a board-to-board connector, so that the ECG chip is electrically connected with the first ECG electrode 20 via the main board and the ECG circuit board 40, and also electrically connected with the second ECG electrode 30 via the second branch 42 and the conductive resilient sheet 50, thereby generating the ECG data according to the electrical signals of the first ECG electrode 20 and the second ECG electrode 30. It is understood that, when the first ECG electrode 20 and the second ECG electrode 30 contact two non-equipotential portions of the user, for example, when the first ECG electrode 20 is touched by the left wrist of the user and the second ECG electrode 30 is touched by the right hand, a voltage difference signal is generated between the first ECG electrode 20 and the second ECG electrode 30, and the ECG chip obtains the voltage difference signal and processes the voltage difference signal into the ECG data.

Further, in order to facilitate the user to view his/her own electrocardiogram, the electronic device 100 further includes a display screen 110 fixed to the middle frame 12 and opposite the back cover 11. The display screen 110 is electrically connected with the main board and configured to receive the ECG data from the ECG chip via the main board and generate a displayable ECG image according to the ECG data. The user may know his own electrocardiogram by observing the ECG image on the display screen 110. Of course, in other implementations, the electronic device 100 may transmit the ECG image to other electronic devices 100 with a display function through communication networks such as Bluetooth, wireless fidelity (Wi-Fi), fifth-generation (5G) wireless communication, and fourth-generation (4G) wireless communication, so that the ECG image may be displayed by an external electronic device with a display function.

Figure 18:
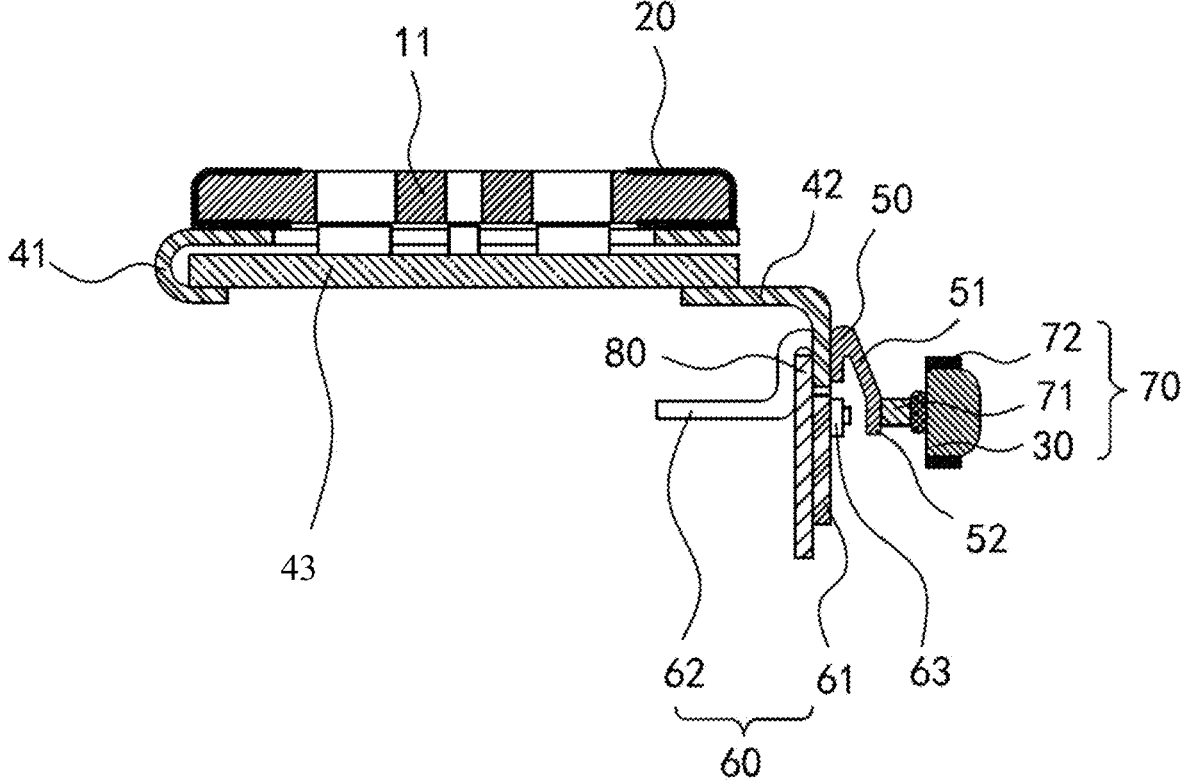
FIG. 18 is a schematic partial cross-sectional view of an electronic device provided in an implementation of the disclosure.

In another implementation, refer to FIG. 18, the implementation illustrated in FIG. 18 is substantially the same as the implementation illustrated in FIG. 16, except that the conductive resilient sheet 50 is fixedly connected with the second branch 42. Specifically, the end of the second branch 42 away from the PCB substrate 43 is attached to a side surface of the circuit board support 80 close to the middle frame 12. The conductive resilient sheet 50 may be bonded to a side surface of an end of the second branch 42 away from the circuit board support 80 via conductive adhesive. The conductive resilient sheet 50 may be connected with a conductive line in the second branch 42 via the conductive adhesive. The fixed base 51 of the conductive resilient sheet 50 is attached to an end of the second branch 42, and the resilient arm 52 extends relative to the second branch 42 and resiliently resists the button column 71 of the side button 70 or the second ECG electrode 30, so that the conductive resilient sheet 50 can make the second branch 42 and the second ECG electrode 30 be in a conducting state. More specifically, in order to increase a structural strength of an end of the second branch 42, the second branch 42 is provided with a reinforcing layer on a side surface of the second branch 42 away from the conductive resilient sheet 50, so that the second branch 42 may effectively support the conductive resilient sheet 50, thereby preventing the second branch 42 from being deformed under a resilient resistance force of the conductive resilient sheet 50, and ensuring safety of the second branch 42. In other implementations, the conductive resilient sheet 50 may also be soldered on the second branch 42.

Figure 19:
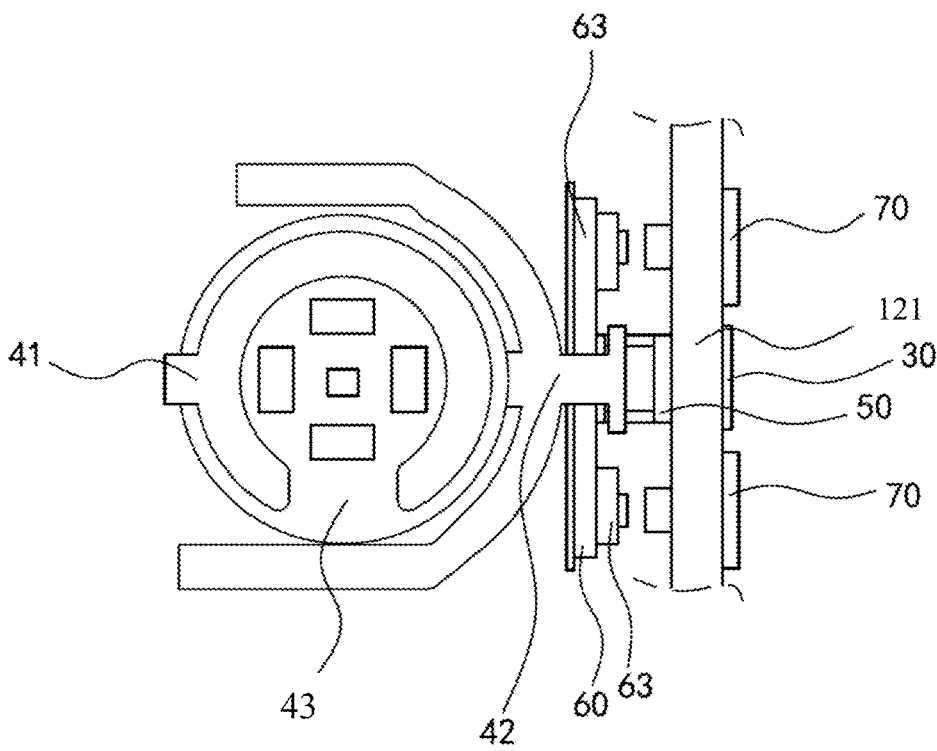
FIG. 19 is a schematic partial view of an electronic device provided in an implementation of the disclosure.

In another implementation, refer to FIG. 19, the implementation illustrated in FIG. 19 is substantially the same as the implementation illustrated in FIG. 16, except that the second ECG electrode 30 is spaced apart from the side button 70, and the second ECG electrode 30 is a metal member embedded in the middle frame 12. The side button 70 and the second ECG electrode 30 are arranged on the middle frame 12 side by side. Specifically, the electronic device 100 is provided with two side buttons 70 at the first side 121, where the two side buttons 70 can be pressed. Two button switches 63 corresponding to the two side buttons 70 are provided on the side-button circuit board 60. The second ECG electrode 30 is disposed between the two side buttons 70. The second ECG electrode 30 is fixedly connected with the first side 121. The second ECG electrode 30 cannot be pressed. The second ECG electrode 30 extends through the middle frame 12, so that the resilient arm 52 of the conductive resilient sheet 50 can resiliently abut against the second ECG electrode 30, that is, the conductive resilient sheet 50 is fixed to the side button 70 at a position between the two button switches 63. The second branch 42 is stacked on the side-button circuit board 60 at a position close to the second ECG electrode 30, so that the conductive resilient sheet 50 can also resiliently abut against the second branch 42. The conductive resilient sheet 50 is separated from the two button switches 63, so that the electrical signals of the button switches 63 will not interfere with the conduction between the second ECG electrode 30 and the first ECG electrode 20.

Figure 20:
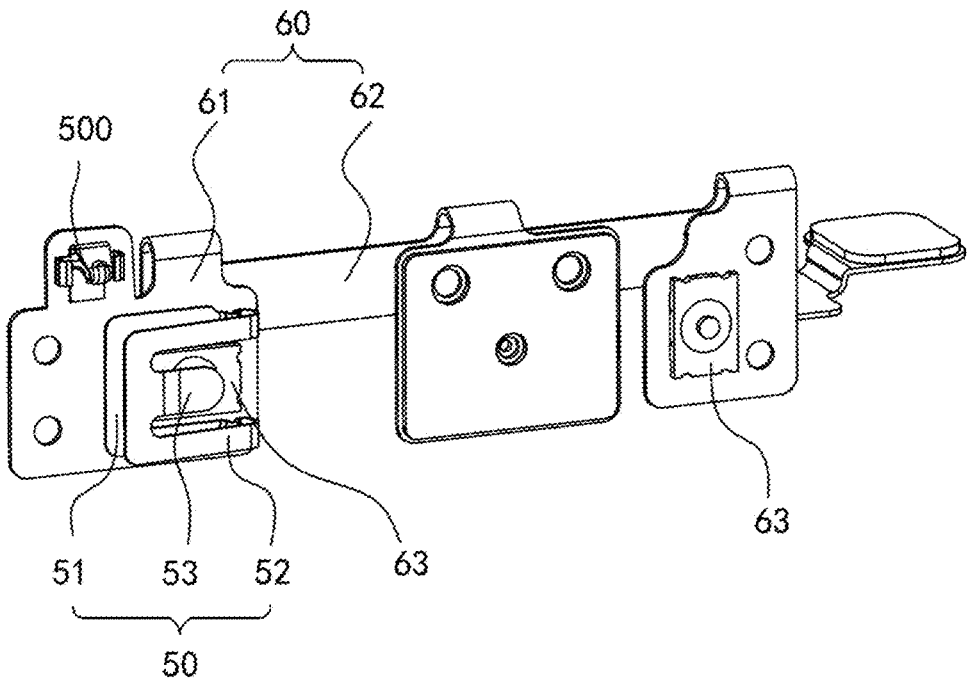
FIG. 20 is a schematic partial perspective view of an electronic device provided in an implementation of the disclosure.

In another implementation, refer to FIG. 20, the implementation illustrated in FIG. 20 are substantially the same as the implementation illustrated in FIG. 10, except that the conductive resilient sheet 50 has a split-type structure. The conductive resilient sheet 50 is further provided with a branch conductive resilient sheet 500 that is fixed to the side-button circuit board 60 and spaced apart from the fixed base 51, and the branch conductive resilient sheet 500 and the fixed base 51 are in a conducting state via the side-button circuit board 60, and the branch conductive resilient sheet 500 elastically resists against the second branch 42. Specifically, a structure of the branch conductive resilient sheet 500 is similar to that of the branch base 54 and the branch resilient arm 55 of the conductive resilient sheet 50 in the implementation illustrated in FIG. 10, except that the branch conductive resilient sheet 500 is spaced apart from the fixed base 51. The fixed base 51 is bonded to the side-button circuit board 60 via conductive adhesive, and is connected with a circuit of the side-button circuit board 60. The branch conductive resilient sheet 500 is bonded with a circuit of the side button 70 via conductive adhesive, and is connected with the circuit of the side-button circuit board 60, thereby realizing a conduction between the branch conductive resilient sheet 500 and the fixed base 51, and thus when the second branch 42 resiliently abuts against the branch conductive resilient sheet 500, the second branch 42 and the second ECG electrode 30 are in the conducting state. The conductive resilient sheet 50 has a split-type structure, so that a volume of the conductive resilient sheet 50 is effectively reduced, facilitating optimization in an arrangement of internal structural components of the electronic device 100. In other implementations, the branch conductive resilient sheet 500 may also be soldered on the side-button circuit board 60, and the fixed base 51 may also be soldered on the side-button circuit board 60.

Figure 21:
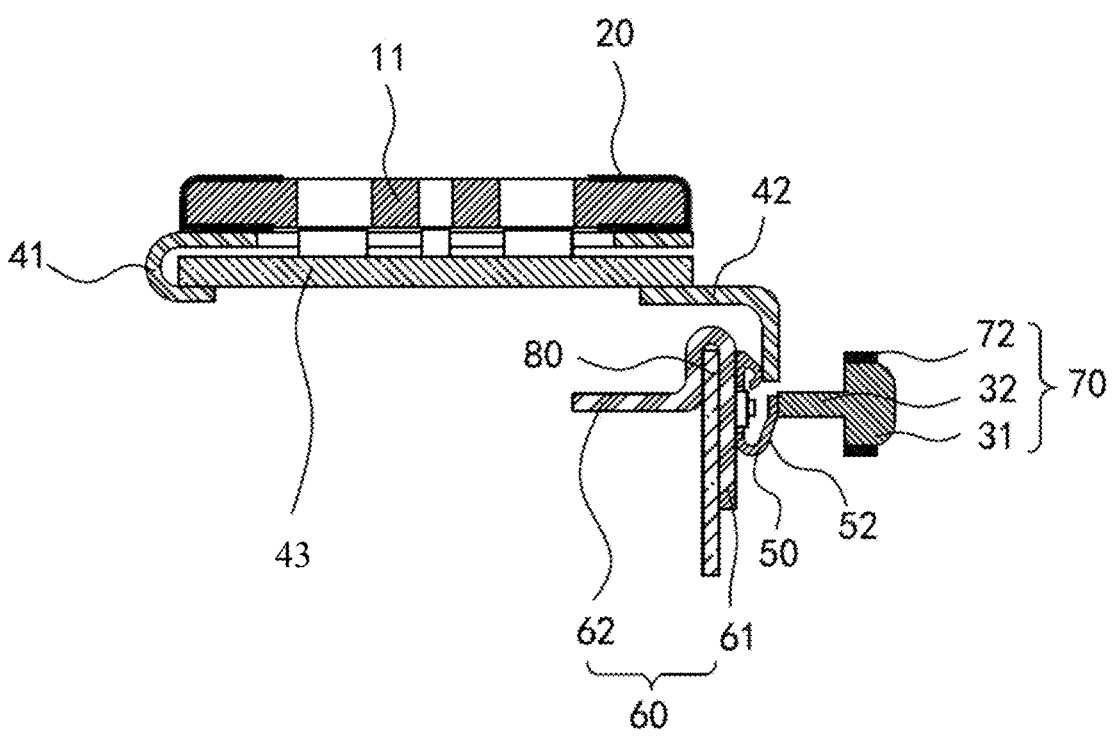
FIG. 21 is a schematic partial cross-sectional view of an electronic device provided in an implementation of the disclosure.

In another implementation, refer to FIG. 21, the implementation illustrated in FIG. 21 are substantially the same as the implementation illustrated in FIG. 16, except that the second ECG electrode 30 is provided with a touch panel 31 disposed outside the middle frame 12 and a conductive column 32 extending from the touch panel 31, the touch panel 31 serves as the button cap of the side button 70, the conductive column 32 serves as the button column 71 of the side button 70, and the conductive column 32 resiliently abuts against the end portion of the resilient arm 52 and is configured to trigger the button switch 63 when the touch panel 31 is pressed. It is understood that, with aid of the conductive column 32 of the second ECG electrode 30, the side button 70 can trigger the button switch 63, so that the conductive resilient sheet 50 directly contacts the second ECG electrode 30, thereby reducing a resistance between the second ECG electrode 30 and the first ECG electrode 20, and improving a conduction sensitivity between the first ECG electrode 20 and the second ECG electrode 30. The insulating cover 72 of the side button 70 is arranged around a peripheral side of the touch panel 31 to isolate the second ECG electrode 30 from the middle frame 12, ensuring that the second ECG electrode 30 may effectively receive touch signals of the user.

Figure 22:
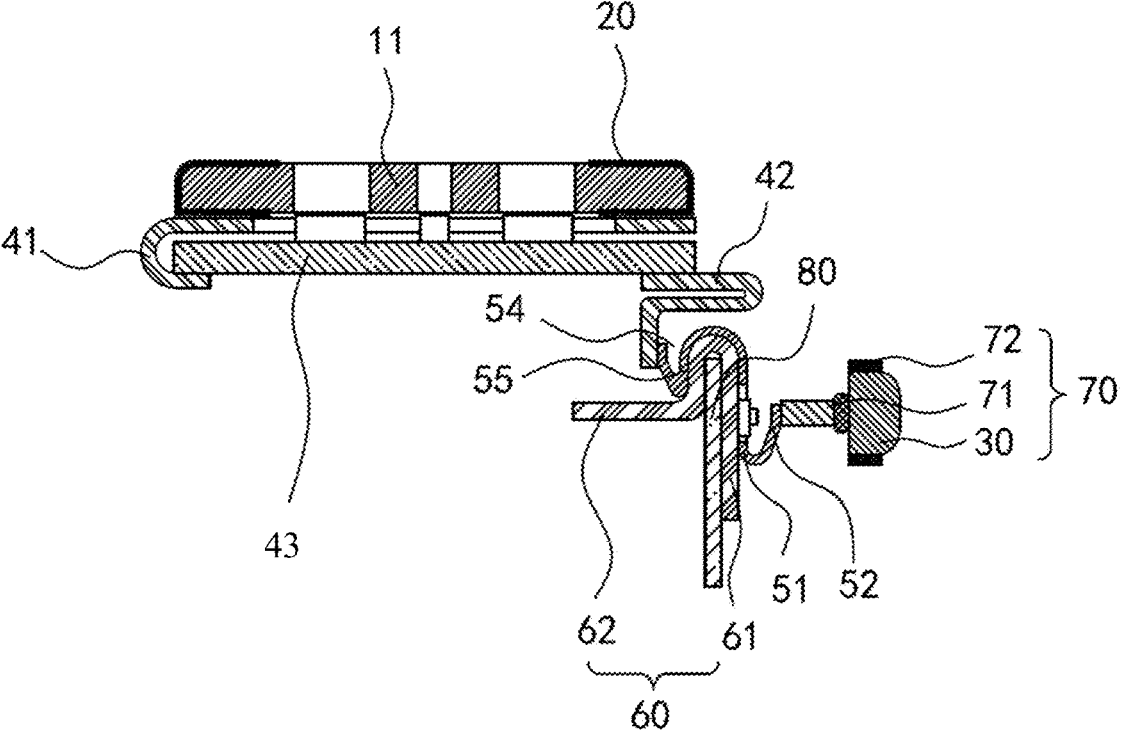
FIG. 22 is a schematic partial cross-sectional view of an electronic device provided in an implementation of the disclosure.

In another implementation, refer to FIG. 22, the implementation illustrated in FIG. 22 are substantially the same as the implementation illustrated in FIG. 16, except that the side-button circuit board 60 is attached to an inner wall of the middle frame 12, an end portion of the second branch 42 away from the PCB substrate 43 is attached to a side surface of the side-button circuit board 60 away from the middle frame 12, part of the conductive resilient sheet 50 is disposed on the side surface of the side-button circuit board 60 away from the middle frame 12 and connected with the second branch 42, and another part of the conductive resilient sheet 50 is disposed on a side surface of the side-button circuit board 60 close to the middle frame 12 and connected with the second ECG electrode 30. In order to shorten the second branch 42, the second branch 42 as a whole is disposed on a side surface of the circuit board support 80 away from the middle frame 12. An end of the second branch 42 is stacked with and spaced apart from the second portion 62 of the side-button circuit board 60, so that the branch base 54 and the branch resilient arm 55 of the conductive resilient sheet 50 can be disposed on the second portion 62 and resiliently resist against the second branch 42. It may be understood that, the fixed base 51 of the conductive resilient sheet 50 is disposed on the first portion 61, and the branch base 54 of the conductive resilient sheet 50 is disposed on the second portion 62, so that the conductive resilient sheet 50 forms a bent resilient piece, that is, the conductive resilient sheet 50 can clamp the first portion 61 and the second portion 62 on the circuit board support 80, so that an effective conduction between the conductive resilient sheet 50 and the second branch 42 can be realized, and structures of the side-button circuit board 60 and the circuit board support 80 can be further stable.

Figure 23:
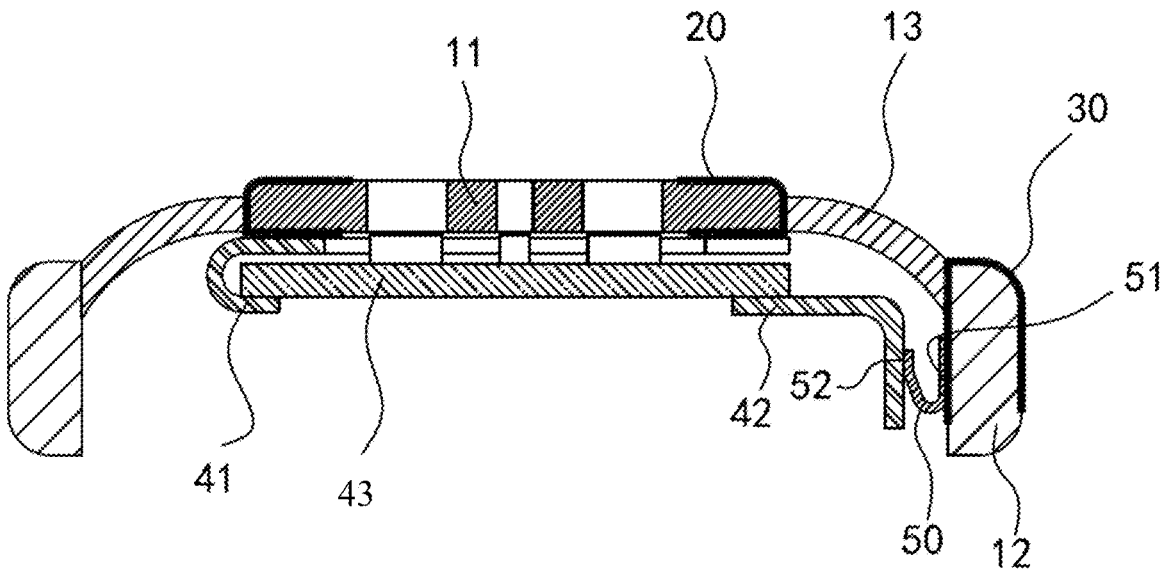
FIG. 23 is a schematic partial cross-sectional view of an electronic device provided in an implementation of the disclosure.

In another implementation, refer to FIG. 23, the implementation illustrated in FIG. 23 are substantially the same as the implementation illustrated in FIG. 16, except that the second ECG electrode 30 is fixed to the middle frame 12 and partially disposed on the inner wall of the middle frame 12, Specifically, the second ECG electrode 30 is a coating layer plated on a surface of the middle frame 12. Another part of the second ECG electrode 30 is plated on an inner surface of the middle frame 12, facilitating the conduction between the second ECG electrode 30 and the conductive resilient sheet 50. When part of the second ECG electrode 30 plated on an outer surface of the middle frame 12 is touched by the user, the second ECG electrode 30 and the user are in a conducting state.

More specifically, the conductive resilient sheet 50 is fixed on the inner wall of the middle frame 12, and is connected with the part of the second ECG electrode 30 disposed on the inner wall of the middle frame 12. Optionally, the conductive resilient sheet 50 may be soldered to the part of the second ECG electrode 30 disposed on the inner wall of the middle frame 12. The conductive resilient sheet 50 may also be bonded to the part of the second ECG electrode 30 disposed on the inner wall of the middle frame 12 via conductive adhesive. The conductive resilient sheet 50 is provided with the resilient arm 52 that may resiliently deform relative to the middle frame 12, and the resilient arm 52 resiliently abuts against the second branch 42, so that the second ECG electrode 30 and the second branch 42 are in a conducting state via the conductive resilient sheet 50, and the closed conduction path between the second ECG electrode 30 and the first ECG electrode 20 can be effectively shortened. The conductive resilient sheet 50 is stably fixed on the inner wall of the middle frame 12, so that the stability of the conductive resilient sheet 50 is improved, the conductive resilient sheet 5 can effectively contact the second branch 42, and conduction between the second ECG electrode 30 and the first ECG electrode 20 is improved.

The above implementations are exemplary implementations of the disclosure, and it is noted that various improvements and modifications may be made without departing from the principle of the disclosure to those of ordinary skill in the art, and the improvements and the modifications are also considered as the protection scope of the disclosure.

What is claimed is:

1. An electronic device, comprising:
a housing comprising a back cover and a middle frame fixed with the back cover;
at least one first electrocardiograph (ECG) electrode disposed at the back cover;
a second ECG electrode disposed at the middle frame;
an ECG circuit board disposed inside the back cover and inside the middle frame, and provided with a first branch electrically connected with the first ECG electrode and a second branch disposed adjacent to and extending toward the second ECG electrode; and
a conductive resilient sheet fixed inside the middle frame and configured to make the second ECG electrode and the second branch be in a conducting state;
wherein the electronic device further comprises a side-button circuit board fixed inside the middle frame, wherein the side-button circuit board and the middle frame cooperatively define a gap therebetween, and an end portion of the second branch away from a printed circuit board (PCB) substrate of the ECG circuit board is disposed within the gap between the side-button circuit board and an inner wall of the middle frame;

wherein the conductive resilient sheet is fixedly connected with the side-button circuit board;

wherein the electronic device further comprises a side button connected with the middle frame and being pressable, wherein the side-button circuit board is provided with a button switch corresponding to the side button;

wherein the conductive resilient sheet is provided with a fixed base close to the button switch and attached to the side-button circuit board and a resilient arm extending from the fixed base in a bent way, and wherein an end portion of the resilient arm faces the button switch and resiliently abuts against the side button;

wherein the conductive resilient sheet is also provided with a branch base extending from the fixed base and a branch resilient arm extending from the branch base in a bent way, the branch base is attached to the side-button circuit board, and the branch resilient arm resiliently abuts against the second branch;

wherein the branch base is provided with two limit buckles opposite each other, an end portion of the branch resilient arm is limited between the two limit buckles and provided with a limit protrusion that is clamped by the two limit buckles, so that the branch resilient arm is prevented from generating plastic deformation.

2. The electronic device of claim 1, wherein the second ECG electrode and the side button are arranged side by side and spaced apart from each other.

3. The electronic device of claim 1, wherein the conductive resilient sheet is also provided with a branch conductive resilient sheet that is fixed to the side-button circuit board and spaced apart from the fixed base, and the branch conductive resilient sheet and the fixed base are in a conducting state via the side-button circuit board, and the branch conductive resilient sheet elastically resists against the second branch.

4. The electronic device of claim 1, wherein the second ECG electrode is disposed at a button cap of the side button, the side button is also provided with a button column fixedly connected with the second ECG electrode, the button column and the second ECG electrode are in a conducting state, and the button column resiliently abuts against the end portion of the resilient arm and is configured to trigger the button switch when the second ECG electrode is pressed.

5. The electronic device of claim 1, wherein the second ECG electrode is provided with a touch panel disposed outside the middle frame and a conductive column extending from the touch panel, the touch panel serves as the button cap of the side button, and the conductive column resiliently abuts against the end portion of the resilient arm and is configured to trigger the button switch when the touch panel is pressed.

6. The electronic device of claim 1, wherein the side-button circuit board is attached to an inner wall of the middle frame, an end portion of the second branch away from a PCB substrate of the ECG circuit board is attached to a side surface of the side-button circuit board away from the middle frame, part of the conductive resilient sheet is disposed on the side surface of the side-button circuit board away from the middle frame and connected with the second branch, and another part of the conductive resilient sheet is disposed on a side surface of the side-button circuit board close to the middle frame and connected with the second ECG electrode.

7. The electronic device of claim 1, wherein the ECG circuit board is fixed inside the back cover, the first branch and the second branch extend out two opposite positions on a peripheral side of the ECG circuit board, respectively, and the first branch is bent relative to a PCB substrate and stacked on the back cover.

8. The electronic device of claim 1, wherein the back cover is provided with two first ECG electrodes, each of the two first ECG electrodes is in a semi-annular shape, and the two first ECG electrodes cooperatively form a substantially annular shape and disposed on a periphery of the back cover.

9. The electronic device of claim 1, wherein the second ECG electrode is fixed to the middle frame and partially disposed on an inner wall of the middle frame.

10. The electronic device of claim 9, wherein the conductive resilient sheet is fixed to a portion of the second ECG electrode disposed on the inner wall of the middle frame and resiliently abuts against the second branch.

11. The electronic device of claim 1, comprising an ECG chip electrically connected with the first ECG electrode and the second ECG electrode, wherein the ECG chip is configured to generate ECG data according to electrical signals of the first ECG electrode and the second ECG electrode.

12. The electronic device of claim 11, further comprising a display screen fixed to the middle frame and opposite the back cover, wherein the display screen is electrically connected with the ECG circuit board and configured to receive the ECG data from the ECG chip via the ECG circuit board and generate a displayable ECG image according to the ECG data.

* * * * *